United States Patent [19]

Zelinka et al.

[11] Patent Number: 4,598,049

[45] Date of Patent: Jul. 1, 1986

[54] GENERAL PURPOSE GENE SYNTHESIZER

[75] Inventors: Richard J. Zelinka, Lino Lakes, Minn.; Keiichi Itakura, Arcadia, Calif.; Carl W. Sims, St. Paul, Minn.; Bruce E. Kaplan, Claremont, Calif.

[73] Assignee: Systec Inc., Minneapolis, Minn.

[21] Appl. No.: 528,053

[22] Filed: Aug. 31, 1983

[51] Int. Cl.⁴ .................. C12M 1/00; C12M 1/36; B67D 5/52; G05B 17/00

[52] U.S. Cl. .................. 435/287; 435/289; 935/88; 436/89; 436/90; 222/137; 525/54.1; 525/54.11; 422/62; 422/111; 422/116

[58] Field of Search ............... 935/88; 422/62, 101, 422/116, 131; 436/89, 90; 435/287, 291, 292, 293, 316, 289; 525/54.1, 54.11; 222/135, 137

[56] References Cited

U.S. PATENT DOCUMENTS

| 3,188,181 | 6/1965 | Peterson | 435/293 |
|---|---|---|---|
| 3,531,258 | 9/1970 | Merrifield | 260/112.5 R X |
| 3,615,235 | 10/1971 | Hrdina | 436/89 X |
| 3,647,390 | 3/1972 | Kubodera | 260/112.5 R X |
| 3,756,920 | 9/1973 | Kelbaugh | 435/291 |
| 3,785,772 | 1/1974 | Coggeshall | 435/293 X |
| 4,106,911 | 8/1978 | Marcelli | 435/287 X |
| 4,192,798 | 3/1980 | Verlander | 260/112.5 R |
| 4,219,530 | 8/1980 | Kopp | 422/69 |
| 4,228,924 | 10/1980 | Gilbert | 222/137 |
| 4,273,261 | 6/1981 | Krueger | 222/135 |
| 4,275,822 | 6/1981 | Juffa | 222/135 |
| 4,353,989 | 10/1982 | Bender | 935/88 X |
| 4,362,699 | 12/1982 | Verlander | 422/113 X |
| 4,483,964 | 11/1984 | Urdea | 935/88 X |

OTHER PUBLICATIONS

Ito, Hirataka et al., *Nucleic Acids Research*, vol. 10, No. 5, 1982, pp. 1755-1769.

Alvarado—Urbina, Gabriel et al., *Science*, vol. 214, 1981, pp. 270-274.

*Primary Examiner*—Robert J. Warden
*Assistant Examiner*—Jeremy Jay
*Attorney, Agent, or Firm*—Orrin M. Haugen; Thomas J. Nikolai

[57] ABSTRACT

A microprocessor controlled, general purpose gene synthesizer for programmably synthesizing selected nucleotide sequences. Depending upon a programmed chemistry, metered volumes of selected bases and reagent/solvents are sequentially metered into the bottom of a reaction cell containing solid-supported nucleotides, where desired linkages are achieved in an agitated suspension. Self-refilling syringe metering and electrically initiated, pneumatically operated valving insures economical, non-contaminated synthesis. Preprogrammed, selectable chemistries and operator programmed sequences are operatively coupled under microprocessor control to ensure a general purpose synthesizer.

22 Claims, 13 Drawing Figures

TYPICAL BASE DELIVERY/REACTION SEQUENCE

DMF WASH SEQUENCE

GENERAL PURPOSE GENE SYNTHESIZER

BACKGROUND OF THE INVENTION

The present invention relates to gene synthesizers and in particular to a general purpose, programmable oligonucleotide sequence synthesizer, operable in response to a pre-programmed linking chemistry and an operator selected nucleotide sequence.

Along with the evolution of an understanding of the function, structure and chemical makeup of nucleotide sequences, such as DNA, so too has an awareness evolved as to the practicalities and feasibilities of genetic engineering. Such engineering efforts, however, require a complete understanding of the chemical and biological reactions in cells. While recent efforts have demonstrated that desired bacterial mutations having desired properties can be engineered, such efforts have been very costly in terms of time, money and equipment.

The most practical of such cellular or genetic engineering efforts, to date, have been achieved via a building block approach that starts with the identification of a desired sequence of nucleotides and progresses to the growth of the desired nucleotide suquences from the component bases; to the modification of identified DNA molecules with the grown sequences; and finally to the seeding of host bacteria with the modified DNA so as to cause the production of the modified DNA via the reproduction of the cells having the sought-after modified DNA characteristics. The success of such processes thus require the linking of a desired nucleotide sequences with appropriately fragmented DNA sequences at desired sites so as to modify the DNA. The modified DNA is then introduced and reproduced by host cells, that are chemically tricked into accepting and reproducing the modified DNA. Such reproduction may also be enhanced via various so called "promotors" which are added to the modified gene. Sufficient quantities of the thus modified genes or protein are then grown via apparatus that promotes the growth of the seeded hosts and at the same time the modified DNA so as to replicate vast numbers of the seeded host bacteria and thereby the modified DNA.

Basic to such genetic engineering efforts is the synthesis of desired nucleotide chains from an initial mononucleotide. In this regard, electro-mechanical apparatus has been developed for synthesizing desired oligonucleotide sequences via the sequential linking of desired bases to a starting or "seed nucleotide." For example, various synthesizing apparatus has been developed by a number of companies, such as the Model 280 synthesizer by Vega Biochemicals, the Model 380A by Applied Biosystems and the DNA/RNA synthesizer developed by the Biologicals Company. The details of such apparatus can be obtained upon reference to the sales literature and various other published literature from these companies as well as upon reference to an article in High Technology, Volume I, No. 1 pp. 60–68 (September/October 1981).

While the above synthesizers offer alternative methods for synthesizing desired nucleotide suquences, each suffers from various shortcomings, such as excessive reagent waste or programming limitations as to the type of chemistry that can be employed. Furthermore, such synthesizers are relatively difficult to operate, maintain and refill with the necessary base/reagent/solvent materials.

The present invention, however, overcomes the above problems and incorporates the above desired features in a general purpose, programmable, microprocessor controlled synthesizer. In particular, the present apparatus is expandable to perform any of the three basic, generally accepted chemistries (i.e. phosphoramidite, phosphate triester or phosphite triester), although the embodiment disclosed hereinafter is of the phosphate type. (A more detailed description of such chemistries can also be found among other places in Nucleic Acids Research Volume 10, No. 5, pp. 1755–1769 (1982) and Hendrickson et al., Organic Chemistry, Chptr. 25-5, pp. 1007–1011 (1970)). Thus, depending upon the selected chemistry and its associated sequence of subroutines, the present apparatus successively meters programmed volumes of the process dependent base/reagent/solvents into a reation cell, and there the desired nucleotide sequences are grown in a liquid suspension on a solidsupport material. While the chemical process may be varied, the present apparatus generally operates to sequentially wash and dry the contents of the cell, expose desired nucleotide reaction sites, add and couple desired bases at the reaction sites and cap or protect the reaction sites, until the next base addition. This process then continues until a desired growth sequence is complete and after which the grown oligonulceotide is chemically separated from the solid support material.

The above objects, advantages and distinctions of the present invention as well as various others will, however, become more apparent upon a reading of the following description and upon reference to the following drawings. It is to be recognized though that while the following description is made with respect to the presently preferred embodiment, various changes (and some of which will be mentioned hereinafter) may be made thereto without departing from the spirit and scope of the present invention.

SUMMARY OF THE INVENTION

A general purpose, programmable oligonucleotide synthesizer. The apparatus essentially comprises a plurality of base/reagent/solvent reservoirs; valve means for steering desired volumes of the base/reagent/solvents per a desired sequence and to selected hydraulic paths; syringe means for metering selected ones of the base/reagent/solvents; a bottom-fed reaction cell containing liquid suspended solid-support materials having seed nucleotides bonded thereto; and a preprogrammed controller means operative in response to a selected chemistry and programmed nucleotide sequence. Additionally, means are provided for agitating the liquid suspended solid-support materials in the reaction cell during the growth process, as well as means for heating the reaction cell so as to promote the growth process.

The controller essentially comprises a programmable read only memory (ROM) and a random access memory (RAM) based program store for containing the pre-programmed chemistries; a RAM memory for containing the operator programmed oligonucleotide sequences; a RAM based processing unit for controlling internal/external communications, sequencing and timing; driver means for actuating selected flow paths; and vibrating and heating means for appropriately promoting chemical reactions. The apparatus also provides for the selective metering of the relatively less espensive base/reagent/solvent materials from relatively large supply reservoirs via pneumatically actuated, chemically inert, pressurized solvent handling valves and conduits and the more expensive materials via a self-filling directional syringe assembly. The syringe assembly, comprises a plurality of syringes coupled to directional valves so as to either permit the metering of a desired volume of base/reagent material into the reaction cell or into the reservoirs supplying the syringe assembly, while ensuring that each of the syringes is refilled during each cycle of each linking sequence. The reaction cell, in turn, comprises a chamber adaptively formed for receiving variously sized and shaped inserts so as to control the internal liquid volume of the cell.

In operation, the base/reagent/solvent materials enter the bottom of the cell and support in suspension appropriate solid-support materials having seed nucleotides attached thereto for appropriate amounts of time. During the coupling time, the associated vibration and heater means, and which too are responsively coupled to the controller, promote the linking of the selected base or bases to the seed nucleotide. Associated waste and test means ultimately collect the waste base/reagent/solvent materials and/or test the waste to determine whether or not appropriate linking actions have occurred. Additionally, the reaction cell is mounted so as to permit an operator to visibly monitor the cell effluent for color and flow during the various control sequences (most typically during detrytilation).

DESCRIPTION OF THE PREFERRED EMBODIMENT

Figure 1:
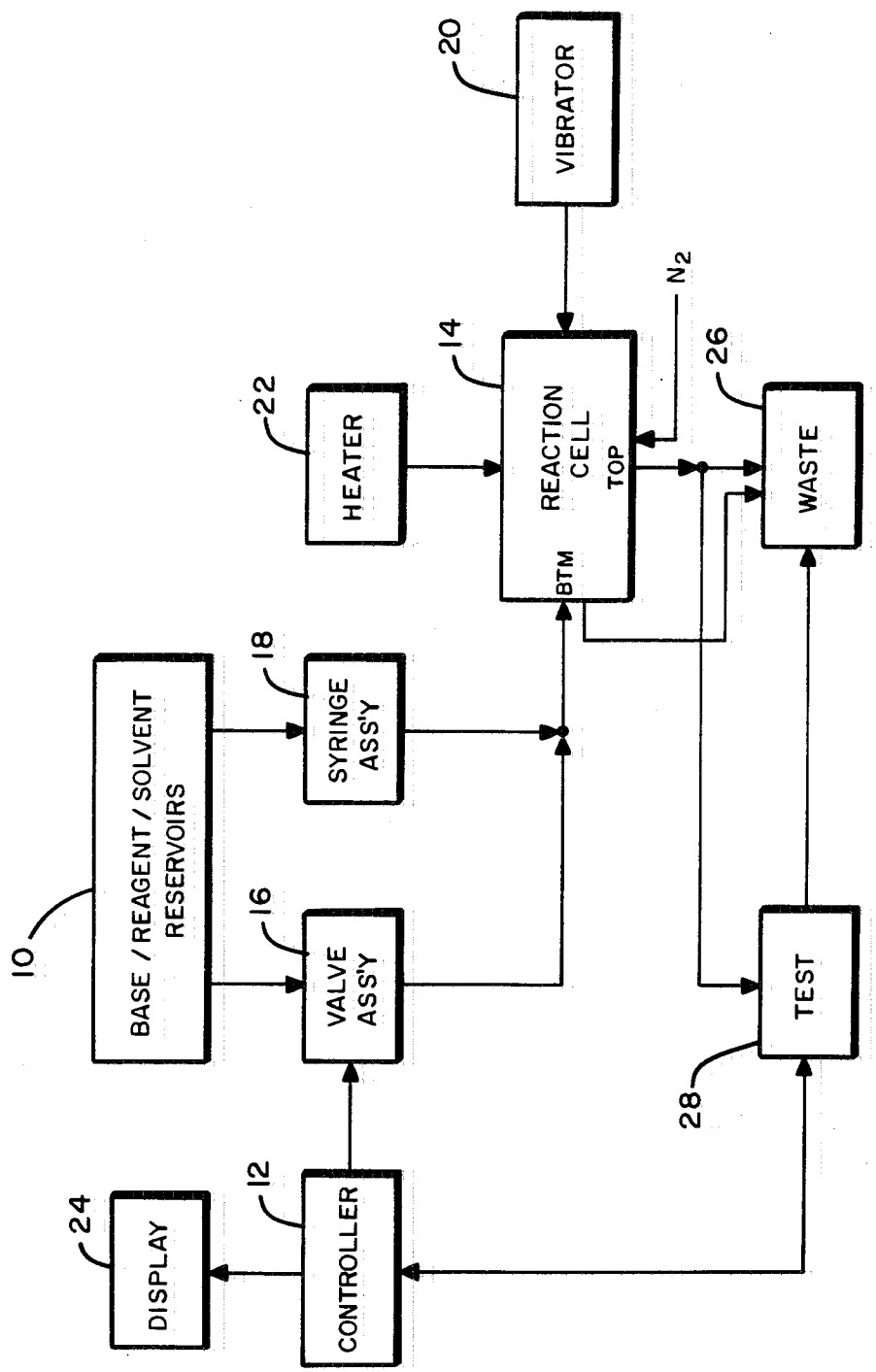
FIG. 1 shows a system block diagram of the present general purpose oligonucleotide synthesizer.

Referring to FIG. 1, a generalized system block diagram is shown of the present synthesizer and which is essentially comprised of a number of base/reagent/solvent reservoirs 10, process controller 12, a bottom-fed reaction cell 14 and associated valve bodies 16 and syringe assembly 18. During normal sequencing, the controller 12 in response to a plurality of pre-programmed subroutines, an operator programmable nucleotide coupling sequence and various process parameters, successively causes the adding of desired bases and reagents to the reaction cell 14 and performs various intermediate solvent washes so as to ensure the uncontaminated growth of the desired oligonucleotide sequence. A vibrator 20 and heater 22 are also included and under the contol of controller 12 promote the linking action. In turn, as the various bases are added to the cell 14 and linked to the seed nucleotides contained therein on a solid-support material the various sequences and valve operations and flow directions are displayed on a display 24. The waste is collected via the waste collector 26 or depending upon the system, test apparatus 28 may earlier sample the waste to determine that the desired reactions have taken place. Alternatively, the reaction cell 14 and portions of the associated low transfer volume clear connecting tubing are visible to the operator on the front panel so as to permit the inspection of the colored reactions and determine whether or not desired reactions have occurred and as evidenced by the coloration of the solution exiting the reaction cell 14. Presently, such visibe monitoring is most often performed during detrytilation; however, due to the length of most sequences, the earlier mentioned use of test equipment is preferred and is achieved via among other appartus, an automatic sampler and associated spectrophotometric test equipment.

While the chemistries employed to promote the linking of desired bases are generally known, although rather complex, the present apparatus simplifies the process by automatically ensuring that the proper base/reagent/solvents are introduced into the reaction cell 14 at the appropriate times and for the proper amounts of time during the growth cycle so as to ensure both the completeness of the reaction and that the proper nucleotide sequence is grown. In fact the present apparatus has been formed to provide a 100% yield in some processes of up to 20 or more linkings. As the proper base/reagent/solvents are introduced into the cell 14, the controller 12 also operates for appropriate amounts of time to cause the vibrator 20 to vibrate or mechanically mix or agitate the granular solid-support material containing the "seed" nucleotides with the introduced base/reagent/solvents so as to make the introduced chemicals available to all the seed nucleotides for optimum chemical reactivity. The heater 22, in turn, is controllably operated for appropriate amounts of time so as to promote the chemical bonding during mixing. It is to be noted though that depending on the chemistry and volatility of chemicals or reaction times, the duration and sequence of heating/mixing may be varied and/or deleted. It is also to be noted the seed nucleotides within cell 14 are generally all of one type so that a number of the desired, identical oligonucleotide sequences are grown at the same time.

The valve means 16 and syringe means 18, like the vibrator 20 and heater 22, are controllably actuated by the controller 12 so as to introduce the appropriate base/reagent/solvents in accordance with the synthesis program and subroutine sequences of Tables 3 and 4 and which will be discussed hereinafter. Depending upon which base/reagent/solvents are selected for a specific sequence, the controller 12 causes the selected base/reagent/solvents to be delivered via associated ones of the valve means 16 and/or the syringes 18 and their associated low dead volume flow paths to the bottom of the reaction cell 14 so to as float in suspension the solid-support material containing the seed nucleotides. At this point, it should be noted that the valves 16 and syringes 18 and their associated flow paths are organized into groups that depend upon the reactivity of the chemicals and which groups are further isolated from one another so as to prevent against unwanted contamination (either in a liquid or vapor form), but which too will be discussed in detail hereinafter. Also, depending upon the cost of the chemicals and the frequency and the volume thereof that is used during normal sequencing, the base/reagent/solvents are either delivered directly from the syringe assembly 18 or from various of the larger pressurized containers 10.

The chemical linkings in the reaction cell 14 thus occur in an agitated suspension. Upon the expiration of each linking period during a series of neutralization and washing steps, the waste chemicals are, in turn, typically flushed from the cell 14 via the introduction of appropriate amounts of solvents and non-reactive materials into the bottom of the cell 14. During the nitrogen (or argon) "blow down" step, however, and which dries the support material with its attached DNA chain following the washing steps, the gas is introduced into the top of the cell 14 and the waste chemicals present in the cell 14 are flushed out the bottom. In all cases the waste chemicals are then delivered to the waste collector 26, except for the detritylation step and for which the chemicals are delivered to an external collector 28 and tested via known techniques and spectrophotometric test and recording apparatus to determine that the desired chemical reaction has taken place.

Simply put, therefore, the present apparatus during each cycle or linking sequence, selectively introduces desired base/reagent/solvents to the reaction cell 14 so as to create a fluidized bed that, in turn, is heated and/or vibrated to promote chemical bonding. Depending upon the chemistry, each cycle or bonding step for each base or mixed-base (including di-mers or tri-mers) proceeds in a similar fashion as dictated by the chemistry, until the desired nucleotide sequence has been grown.

Figure 2:
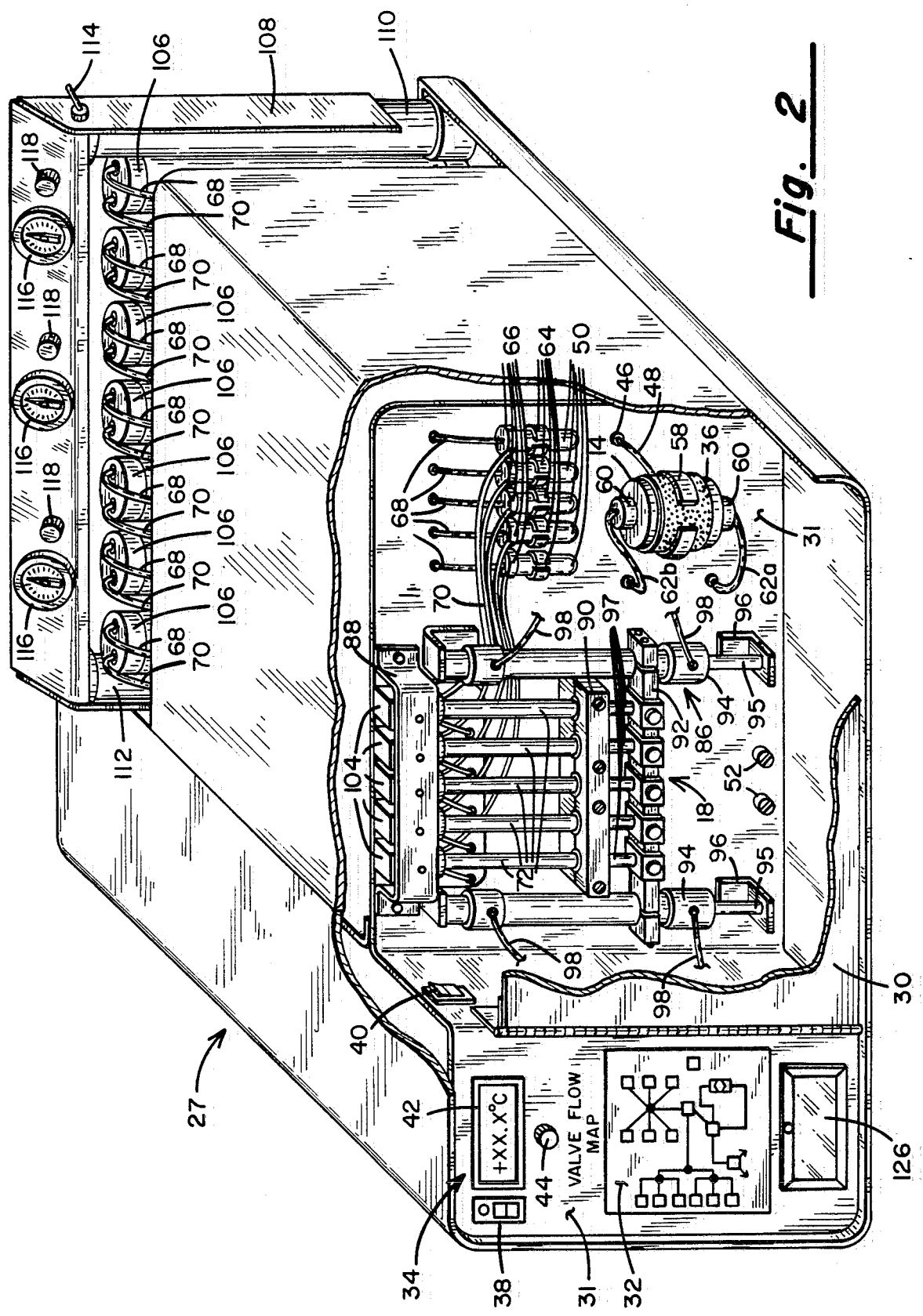
FIG. 2 shows a perspective view of the primary mechanical elements contained in the present apparatus.

Referring now to FIG. 2, a partially sectioned perspective view is shown of the present apparatus with various portions of the cabinet 28 and its front cover 30 removed. From this view, the primary elements of the present synthesizer can be seen in their relative positionings with respect to one another and the metal cabinet 28. In particular and looking to the normally exposed portion of the front panel 31, only the back-lighted hydraulic flow map 32 and temperature controller 34 are visible to the operator. While the flow map 32 will be discussed in greater detail hereinafter as it relates to the front panel, it generally comprises a back lighted display 32 whereon the various pressurized syringes, reservoirs and valve bodies are shown so as to provide the operator with a visible indication of what reservoirs and flow paths are selected and are operational at any point in time. Thus, the operator can, at a glance, determine what portion of the synthesis cycle is active.

The temperature controller 34, in turn, provides the operator with pertinent temperature information as it relates to the reaction cell 14 and whether or not heat is being applied. The temperature controller 34 will, however, not be described in any detail, since it too is the subject of a presently co-pending patent application (i.e. Serial No. 06/377,627), assigned to the present Assignee. Suffice it to say that the temperature controller 34 generally monitors the temperature of the reaction cell 14 and which is heated by an epoxy encapsulated thin film heater/sensor element 36 that is wrapped about the reaction cell 14. The temperature of the reaction cell 14 is set and read via a set/read switch 38, while the power to the controller 34 (including all over circuitry) is applied via an on/off switch 40. The temperature, in turn, is displayed on a liquid crystal display 42 and which also displays the "set" temperature as it is adjusted via the adjustment knob 44. Power, on the other hand, is applied to the thin film heater/sensor 36 and reaction cell 14 via plug jack 46 and multiwire conductor 48 so as to ensure that the fluidized bed within the reaction cell 14 is subjected to desired temperatures during the appropriate phases of each cycle.

Referring now to the various apparatus attached to the internal recessed portion of the front panel 31, this portion of the panel 31 generally contains a plurality of syringe bodies or assemblies and associated supply reservoirs in the form of reagent vials 50, along with the reaction cell 14 and syringe speed of movement adjusting screws 52. These latter adjusting screws 52 are used to regulate the air flow from the pneumatic cylinders that are used to control the movement of the syringe plungers 97. The overall system air presure, in turn, is provided in a range on the order of 45 to 60 psi. and is used to operate the various pneumatically actuated mixing/delivery valves and air actuator that too will be described in detail hereinafter.

Turning attention to the reaction cell 14, it is removably mounted to the front panel 31 via a specially designed clamp or holder 58 which, in turn, is coupled to a vibrating means (not shown) that is mounted behind the panel 31. Thus, the clamp 58 and cell 14 vibrate upon actuation of the vibrator means. This mode of agitation is felt to be preferable to that offered by other manufacturers in that it minimizes the complexity of the apparatus and in conjunction with the fluidized bed ensures the exposure of all the base seeded resin particles to the dissovled solvents/bases/reagents. It is also to be noted that the vibrator is attached to the cabinet 27 via well known dampening bumpers so as to minimize any undesired vibration that might otherwise be induced in the panel 31 or cabinet 27.

Attached to the top and bottom of the cell 14 are, in turn, a pair of threaded couplers 60 which couple the supply and waste tubing 62a and 62b to the cell 14 in a compression fit fashion. While other known means of attachment are acceptable, it should be noted that the tubing 62 as well as all other chemical containing tubing of the present apparatus should be of a low dead volumn type such as for example a teflon tubing having a 0.020 inch I.D. Such tubing has been found to be capable of withstanding operating pressures and minimizes the wasting of the chemicals.

Figure 3:
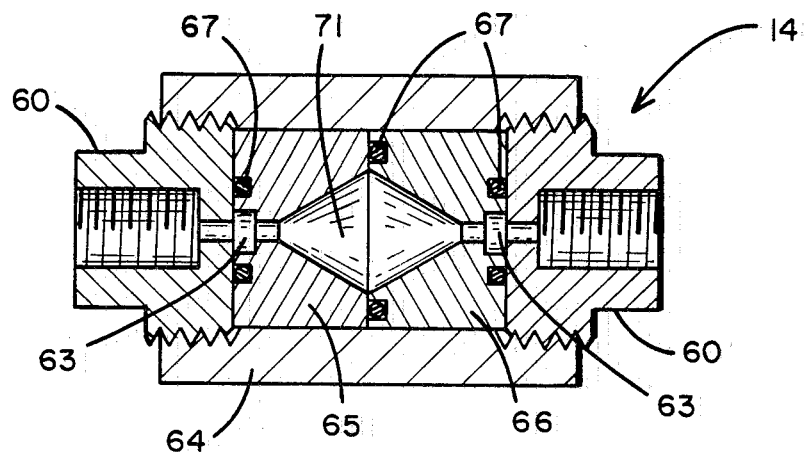
FIG. 3 shows a detailed cross sectional view of the reaction cell.

Attention is now also directed to FIG. 3 wherein a detailed cross-sectional view is shown of the reaction cell 14 along with its various components. Generally, the reaction cell 14 is fabricated from an appropriate non-reactive, heat transferring material, such as type 316 stainless steel, and is formed to permit the disassembly and changing of the liquid volume size of the cell 14. In particular, the cell 14 is comprised of a body member 64 that is threaded to receive the upper and lower fittings 60 and tubing 62. Between the fittings 60, the cell 14 contains removable inserts 65 and 66, each of which have grooves formed therein for receiving "O" rings 67 at the interfaces between the couplers 60 and the inserts 65 and 66 and frits or filters 63 at the top and bottom. The inserts 65 and 66, are presently formed so as to create a frustoconical chamber 71, but it is to be recognized that various other chamber shapes and sizes are easily achieved by varying the manufacture of inserts 65 and 66. The chambers 71 as presently available are also sized to contain liquid volumes on the order of 100 microliters to 500 microliters. The cell inserts 65 and 66 are also conveniently formed so as to allow the direct weighing of the seeded resin in the cell 14 prior to beginning a synthesis sequence, thus minimizing handling.

At this point, it should also be recognized that while the present description is made with respect to a single reaction cell 14, conceivably a number of such cells could be coupled to the present apparatus. Each such additional cells 14 could then, too, either be vibrated and/or heated as desired and within which identical or different sequences could be grown, depending on the programming of the controller 12. Such additional cells 14 then, too, could be operated in parallel or sequentially so as to optimize the through-put of the present apparatus.

Returning to the description of FIG. 2 and with continued attention to FIG. 1, mounted immediately above the reaction cell 14 are a number of reagent vials 50 and which are used as supply reservoirs for the syringes 72 of the syringe assembly 18. The reagent vials 50 are mounted to the front of the panel 31 in a removable fashion via a plurality of holders 64 and which facilitate the removal and refilling of the vials 50, at or near depletion. The vials 50, in turn, each contain a cap having a septum sealed syringe port and pressurized lines 68 coupled thereto so as to facilitate the flow of the base/reagents into and out of the vials 50 via color coded fluid lines 70. It is to be noted that dry nitrogen or argon is used as the pneumatic medium for pressurizing the reservoirs 10, including the vials 50, and which is chemically inert to the various chemicals used with the present equipment.

Figures 4A, 4B:
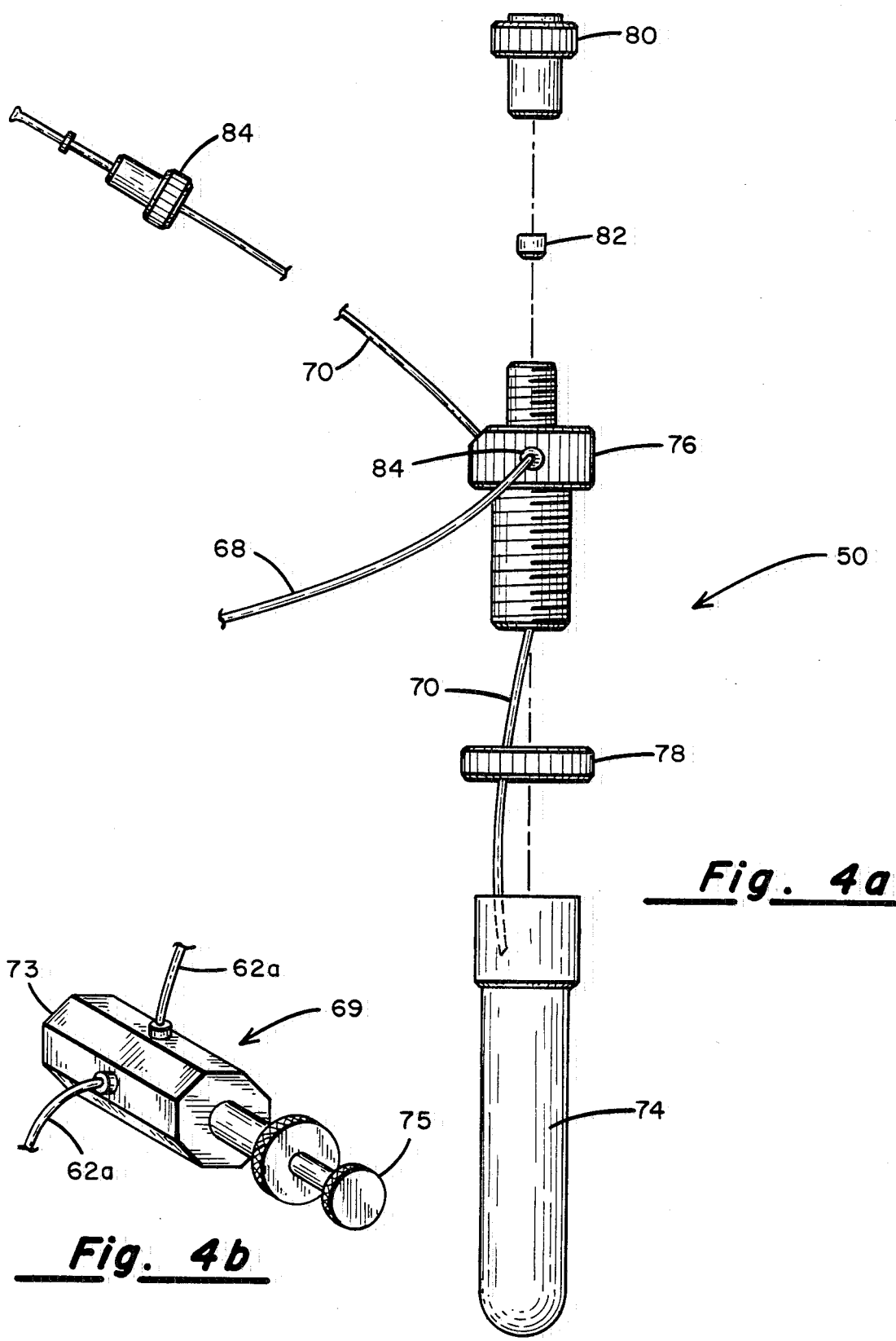
FIG. 4a shows a detailed exploded view of the vial reservoirs.
FIG. 4b shows a perspective view of a typical septum port injection which may be added for di-mer or tri-mer containing processes.

Directing attention to FIG. 4a, a detailed and disassembled view is shown of the present syringe supply vials 50. Specifically, each of the vials 50 is comprised of an elongated, test tube-like, glass vial body 74 into which a threadably secured syringe port 76 is secured via a lock nut 78. A septum cap 80 and septum 82 are, in turn, threadably secured into the top of the syringe port 76 and which permit the refilling of each vial body 74 without discontinuing operation of the present equipment. Completing the structure of each vial 50 are associated compression fittings 84 for compressably securing the pressure lines 68 and fluid lines 70 to the syringe port 76. It is to be noted, too, that while the pressure lines 68 terminate at the syringe port 76, the supply lines 70 extend into the glass vial body 74 so as to submerge the inlet to the fluid lines 70, thus ensuring proper liquid pick-up.

FIG. 4b on the other hand shows a perspective view of a septum port injector 69 such as manufactured by Scientific Systems, Inc., and which although not shown in FIG. 2 may be added as desired. Such an injector 69 is comprised of a body 73 containing a septum (not shown) that is accessible to a syringe inserted through the threaded closure stem 75. In operation, one or more of such injectors 69 may be added to the panel 31 in series in the supply line 62a to the reaction cell 14 or be isolated from one another so as to permit the injection of separately prepared di-mers or tri-mers of the bases into the reaction cell 14. Thus, the possible linking sequences can be further expanded, as well as the possible length of any given sequence and which could thereby be extended to 80 bases, if di-mers are used (such being the case since depurination has typically been encountered at 40 or more linkings).

Also, assuming the use of the septum port injectors 69, it then becomes possible to couple automatic injectors thereto, such as are used in high performance liquid chromatography (HPLC). Such injectors would further automate the present apparatus and permit fully automatic control as where the chemicals are arranged in a desired order relative to the injectors and which would appropriately be activated by the controller 12 relative to the programmed chemistry.

Returning again to FIG. 2 and mounted to the left of the vials 50 is the syringe assembly 18, and which is comprised of five or more syringes 72 that are mounted in a pneumatically driven rack 86 and which rack, in turn, is comprised of a valve body containing base member 88, syringe body holding member 90 and a plunger driving member 92. The driving member 92 is retractably mounted to right and left pneumatic cylinders 94, while the holding and driving members 88 and 90 are stationary. Each of the pneumatic cylinders 94 also have associated supply and return air pressure lines 98 and which are, as mentioned, interactively controlled via the speed adjusting screws 52 so as to permit the calibration and regulation of the exhaust air flow from the cylinders 94. Also associated with each of the push-rods 95 of the cylinders 94 are length adjusting means (not shown) and which in conjunction with the lower stationary "L" brackets 96 permit the adjustment of the length of throw of the cylinders 94. Thus, as air pressure is applied in either direction to the cylinders 94, the cylinders 94 raise or lower and thereby depress or retract the plungers 97 so as to deliver or recharge each of the syringes 72 with a known volume of chemicals.

Figure 5:
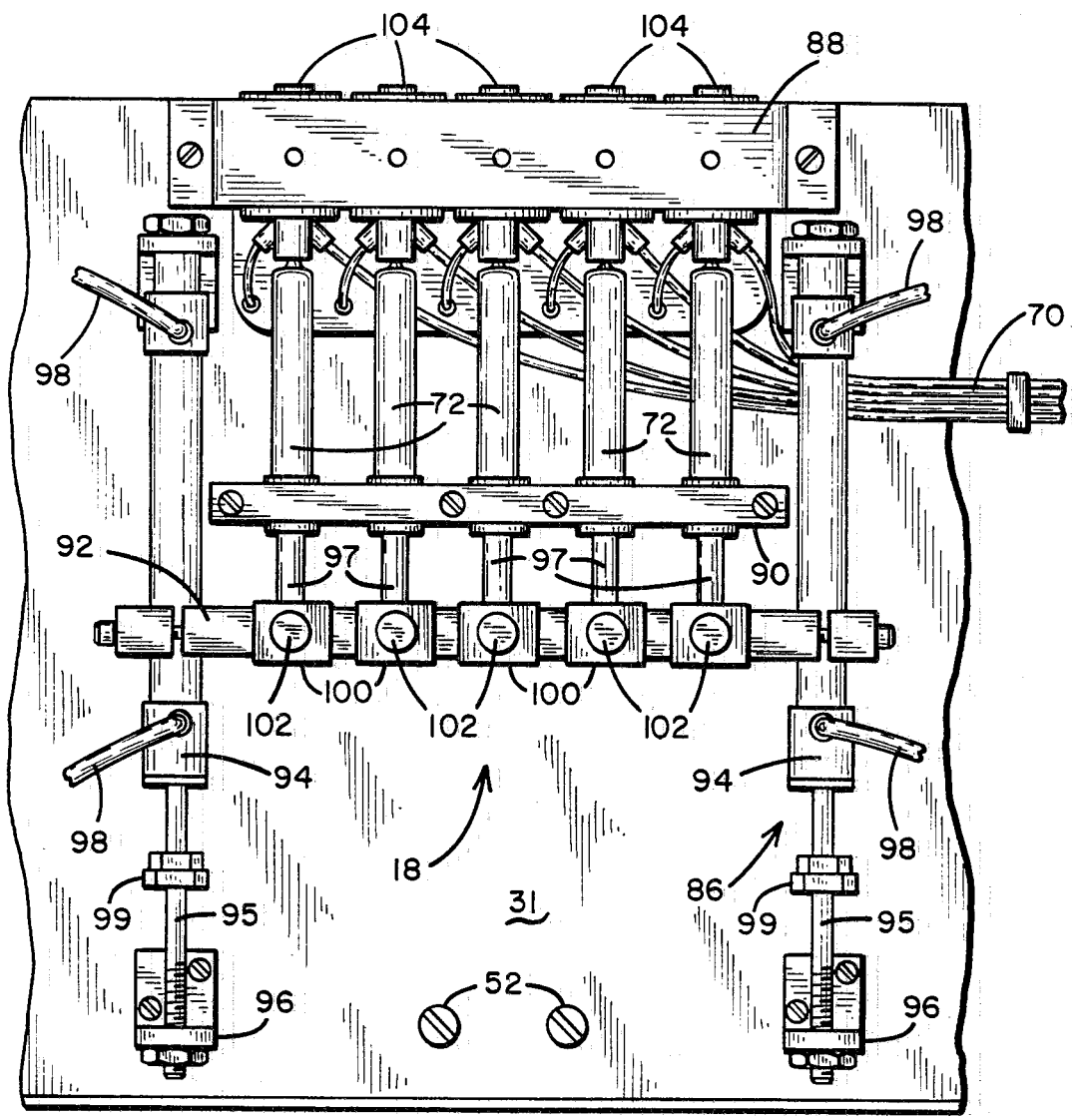
FIG. 5 shows a detailed view of the syringe body.

For a more detailed view of the syringe assembly 18, attention is also directed to FIG. 5. From FIG. 5, the compression mounted cylinder travel adjusting nuts 99 are shown in detail relative to the push-rods 95 and the stationary L brackets 96 and their associated mounting hardware, (i.e. screws, rivets, etc.). Upon reference also to the syringes 72 and the various support members including holding members 88, 90 and plunger driving member 92, it is to be noted that the plungers 97 of each of the syringes 72 are mounted to the driving member 92 via separate clips 100 and knurled thumb screws 102 that are threadably secured to the driver member 92. Each of the heads of the plungers 97 are rigidly contained beneath one of the clips 100 via an associated thumb screw 102. Thus, as the plunger driving member 92 (and which is attached at its right and left ends to the cylinders 94) moves with the cylinders 94 so, too, do the syringe plungers 97 move in and out of the syringe bodies 72.

The syringe bodies 72, in turn, are mounted to the panel 31 via the two-part or split holding member 90, and which can be disassembled so as to permit the insertion and removal of the individual syringe bodies 72. It is to be noted, too, that each of the syringe bodies 72 are frictionally mounted within holes bored between the two halves of the holding member 90 via appropriate resilient interface material, such as split rubber or plastic bushings. The tips or nozzles of the syringe bodies 72 are, in turn, each coupled in a threaded fashion to an individual pneumatically actuated valve body 104 that is mounted to the back of the holding member 88.

Referring next to the valve bodies 104, in the preferred embodiment they are each typically comprised of a pneumatically actuated three-way valve and are each operable via an electrically driven solenoid that supplies air pressure to the actuator of the valve body 104. The valves 104 may, also each be operated manually to confirm operability via switch handles (not shown) that are mounted to the backs thereof. At normal operating pressures, though, the valves 104 do not permit manual actuation. In particular and during normal operation, the controller 12 acts through a plurality of associated electro-pneumatic solenoids (not shown) to pneumatically actuate and select only desired ones of the valve bodies 104, such that only the base/reagent contained within a selected syringe 72 is supplied via the selected valve body 104 to the reaction cell 14. At the same time, however, the others of the non-selected valve bodies 104 and syringes 72 are also actuated so as to return an equal amount of base/reagent via their associated supply lines 70 to their associated reservoir vial 50. After each syringe delivery of chemical, the controller 12 then selects all the valve bodies 104 and retracts the plunger drive member 92 so as to refill each of the syringes 72. Thus, measured volumes of base/reagent are economically supplied to the reaction cell 14 as needed during each growth cycle without wasting any of the rather costly chemicals.

It is also to be noted that at present the operator must periodically monitor the base/reagent/solvent containing supply reservoirs 106 so as to confirm whether or not they are near depletion. If they are near depletion, they must be refilled and which in the case of the supply reservoirs 50 merely requires injecting more chemicals through the septum cap 80. Alternatively, an alarm condition may be implemented to warn the operator and which would sound when the controller 12 confirmed that its record of base/reagent delivered to date exceeds a predetermined limit. In the latter event, upon refilling the vials 50 and clearing the alarm, normal operation would resume and each syringe 72 would continue to be refilled from its associated vial 50 at the end of each cycle.

Before continuing, it should be noted, too, that in the event of a power failure, the present apparatus is programmed to repeat only the last step performed or during which the power failed. Thus, while extra chemicals might be consumed in the repeated step, the sequence in process is not wasted. Also, it should be noted that provision has been made for saving any operator programmed information in the event of a power failure for up to approximately four hours so as to prevent against having to reprogram.

Returning again to FIG. 2, it is to be noted that a number of relatively large containers or reservoirs 106 have been mounted in to the back of the present synthesizer. These, typically, each contain one liter or 500 milliliters of a number of relatively less expensive chemicals, such as the solvents, and which containers 106 too are each pressurized via individual dry nitrogen or argon pressure lines 68. As with the vials 50, associated color coded supply lines 70 are, in turn, coupled from the containers 106 to various other three-way valve bodies 104 (not shown) that are represented on the hydraulic flow map 32 and which are mounted behind the panel 31. The specific groupings of valve bodies 104 associated with the base/reagent/solvent containing supply reservoirs 50 and containers 106 and the fl ow therebetween will however be described in greater detail hereinafter. It should also be noted that the containers or reservoirs 106 are pneumatically mounted on a rack 108 via air cylinders 110 and 112 so as to be simultaneously raised or lowered upon actuation of the raise/lower toggle switch 114. Also, mounted on the top of rack 108 are a number of pressure gauges 116 and regulator knobs 118 for controlling the nitrogen pressure on the reservoirs via pressure lines 68.

While to date and as mentioned a number of delivery approaches have been suggested, it should be apparent from the above that the present delivery system, due to the simplicity of its mechanical configuration, requires a minimum number of operating control functions and circuitry. Also, due to the use of low transfer volume delivery lines 70 and syringes 72, the amount of chemicals used per linking sequence is minimized. Similarly, the vibrating and heating of the reaction cell 14 facilitates linkage and permits a reduction in the amount of chemical used over the other known synthesizers as well as overall cycle time. Thus, the present apparatus permits the bio-engineer to efficiently and economically grow any desired oligonucleotide sequences.

Before continuing, it should be noted that while parallel coupled syringes of the present type are believed to provide the most efficient delivery mechanism for DNA synthesis, alternatively and for other synthesis activities larger volumes of chemicals may be required. Therefore, it is contemplated that other types of rate controlled pumps could be employed with modification of the present assembly to provide appropriate agitation of the chemicals and sufficient synchronization between the controlled pumps. Further, it is to be recognized that for some applications it may be advantageous to separately control the individual syringes 72 or pumps.

Figure 6:
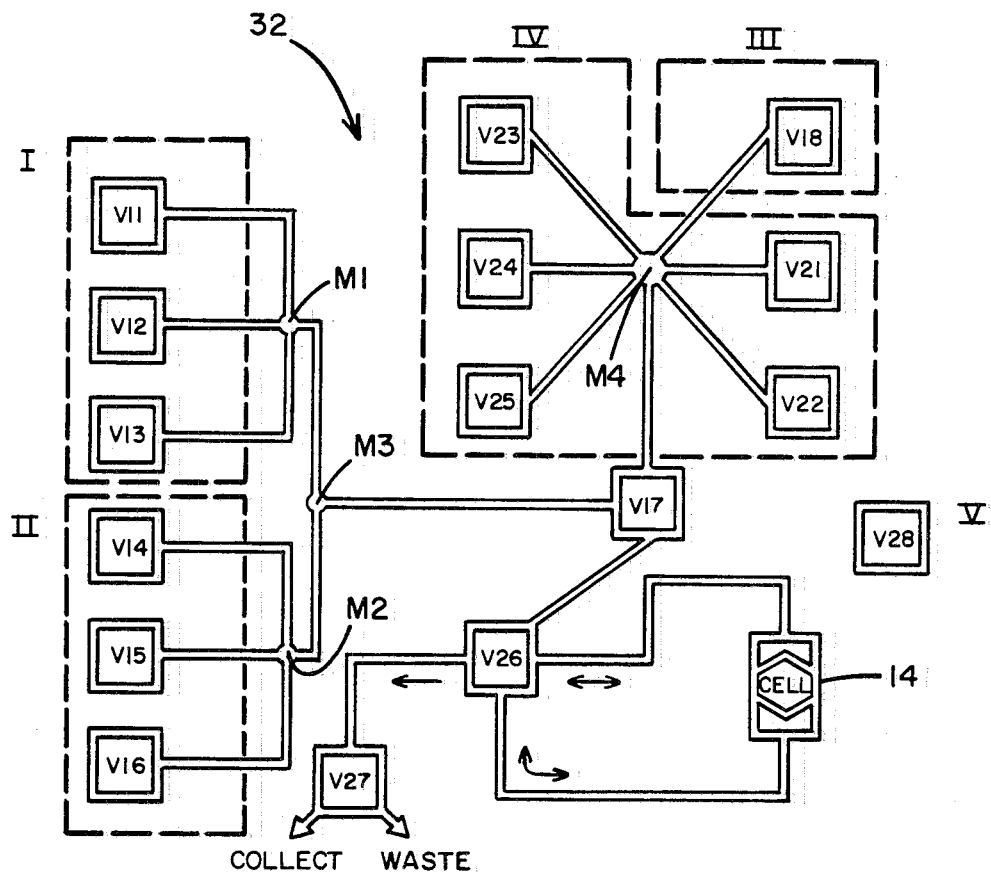
FIG. 6 shows the hydraulic flow paths for the base/reagent/solvent materials as they traverse the various valves and syringes.

Referring now to FIGS. 6 through 10, a more detailed description will follow as to the control circuitry and operation of the present apparatus during its various subroutine sequences. In particular and referring to the hydraulic flow map 32 of FIG. 6, it is to be noted that the flow map 32 is partitioned to shown the previously mentioned chemical groupings and the correlation between the various valve bodies 104, solvent bottles 106, and syringes 72 as well as the points of isolation therebetween. Isolation is required to ensure that the base/reagent/solvents aren't contaminated with non-compatible base/reagent/solvents prior to delivery to the reaction cell 14. In particular, the valve bodies 104 associated with the solvent bottles 106 are divided into three groups I, II, and III; while the valve bodies 104 associated with the syringes 72 comprise a fourth group IV. Specifically, the valve bodies 104 labeled V11 to V16 and V18 are each associated with one of the solvent bottles 106 of groups I, II and III; while the valve bodies 104 labeled V21 to V25 are each associated with one of the syringes 72 of group IV; and while the valve bodies 104 labeled V17, V26 and V27 control the flow of the base/reagent/solvents to the cell 14 and waste. Finally, the valve body 104 labeled V28 controls the air supply to the syringe assembly 18 and regulator screws 52. FIG. 6 thus essentially sets out a hydraulic flow map and the fluid flow path of the chemicals from the valve bodies 104 to the reaction cell 14.

Before continuing, it should be recalled that numerous chemistries may be implemented with the present synthesizer, although for purposes of the present description the phosphotriester chemistry has been chosen to hereinafter represent the functions of this instrument. Therefore assuming a configuration operating in response to a controller 12 programmed with the phosphotriester chemistry, the containers or reservoirs 106 associated with the valve bodies V11 to V16 and V18 would each respectively contain zinc bromide ($ZnBr_2$) (or other "trityl" rem oving chemical) methylene chloride ($CH_2Cl_2$), dimethyl formamide (DMF), acetonitrile, capping reagent No. 1, capping reagent No. 2 and pyridine. The valve bodies V21 to V25 associated with the syringe assembly 18, on the other hand, would each respectively contain MSNT (or other coupling reagent) and the four bases—guanine (G), cytosine (C), adenine (A) and thymine (T)—and each of which bases have been chemically altered to make the bases chemically reactive. Also, it is to be kept in mind that during a typical cycle or sequence of subroutines (each containing a number of steps), the present apparatus as it dispenses the above chemicals generally operates to perform a series of solvent washings with intermediate flushing subroutines so as to: (1) clean the reaction cell 14 and the base-seeded solid support material or resin and prepare it for the addition of the next selected one or more base nucleotides; (2) add an operator selected one or combination of base nucleotides; and (3) perform a series of post addition subroutines (i.e. syringe refresh, pyridine wash/nitrogen blow down, cap and end). Each of the various subroutines for a typical cycle of the phosphotriester chemistry will, however, be described in greater detail hereinafter.

From FIG. 6, it generally is to be recognized that as the various valve bodies 104 are enabled, the liquid flow paths from groups I, II, III and IV all converge at valve body V17. Prior thereto, however, each of the groups are coupled together via appropriate manifold assemblies M1, M2, M3 and M4. Manifolds M1 and M2 are each of a 3×1 configuration, while manifold M3 is of a 2×1 configuration and manifold M4 is of a 6×1 configuration. Each of the manifold assemblies thus accommodates a number of chemical inputs which are coupled via independent flow paths to a common point so as to provide a single output. It is to be recalled that chemical and gaseous isolation is desired between various of the groups so as to prevent intergroup contamination and this is achieved via the various manifold assemblies. In particular, the outputs of manifold M1 and M2 are coupled to a third manifold assembly M3 such that due to the equalized nitrogen pressure of the system on each of the manifold inputs, the chemicals of group I are isolated from group II. Similarly, the chemicals of groups III and IV are isolated from one another via manifold assembly M4; while groups I and II are isolated from groups III and IV via valve body V17. It is to be recognized, though, that while manifold assemies are used in the present embodiment, additional valve bodies 104 may be used in lieu of manifold assemblies M1 to M4 to provide chemical isolation, but that such valve bodies 104 would entail some further control.

From the above, it should be apparent that further isolation is also achieved via valve body V17 and which essentially acts as a clearing or selector valve for the various solvent bottles 106 of groups I, II and III and the syringes 72 of group IV. That is, upon the enabling of the valve body V17, only one or the desired simultaneous combination of the solvent/reagents from groups I to IV is selected and directed to valve body V26. There, depending upon the position of valve body V26, the liquid is again selectively directed either through reaction cell 14 to valve body V27 and then to collection or waste; or is blocked from flowing through cell 14 and in which case a nitrogen or argon gas purge is directed from the top of the cell 14 and waste is purged from the bottom of the cell 14. In this fashion, valve bodies V17 and V26 provide selective three-way control and ensure that the liquid chemicals generally enter the reaction cell 14 from the bottom and leave from the top so as to further agitate the contents of the reaction cell 14 during normal liquid flow. (Only during a blowdown operation is sequence reversed.) It should also be apparent that via the vibrator 20, no elaborate mechanical linkage is necessary with the present apparatus to agitate the contents of the reaction cell 14. This is not the case, however, with other known equipment which either do not agitate the reaction cell or shake the reaction cell up and down or variously rotate it, as with one known device which alternately turns the cell 180°.

As mentioned, the liquid flow paths of the present system are pressurized with chemically inert, dry nitrogen or argon gas that is regulated to approximately 12 to 25 psi. Therefore, as each of the various valve bodies 104 are selected and depending upon the duration of the enabling signal and pressure applied to the reservoir vessel, an appropriate volume of liquid chemical flows in the selected flow path to the reaction cell 14 via valve bodies V17 and V26. As the base/reagent/solvents are flushed from the cell the waste material is then directed via valve body V26 to valve body V27. There, the waste material is either directed to the test collect station 28 or to waste 26.

Although, during nitrogen or argon blow-down operations valve V26 stops fluid flow from valve V17 and directs the gas from the top to the bottom of the cell 14, thereby assisting in the washing and drying of the material in cell 14. For automated systems, it is to be noted that an automated test collection stand may be used in conjunction with valve body V27 and which is appropriately enabled at various points in time to advance and collect the backflushed chemicals from valve body V27. Most typically though such collections are taken only during one step for each cycle and which typically is that step following the admitting of the zinc bromide or other detritylating reagent. In this fashion, the operator may, subsequent to a linking sequence, test the various collected samples to determine if appropriate linkings took place and whether the quantity of the grown sequence is sufficient for laboratory use.

As mentioned, the present apparatus is preprogrammed with a plurality of subroutines, all of which are operator selectable, for bonding desired bases or combinations thereof during each cycle as per the programmed chemistry. In this regard a portion of the subroutines are directed to the necessary process steps for the programmed chemistry, while the remainder of the subroutines are concerned with the base addition sequences, once the chemistry has been established. While the various subroutines for the phosphotriester chemistry will be discussed in detail hereinafter, for the moment it is to be recognized that once the chemistry has been selected and the associated subroutines defined, the operator thereafter need only program the desired oligonucleotide sequence via a multi-step listing that specifies the various base sequence subroutines to be accessed, since all necessary chemical additions, timing, etc. will thereafter be performed pursuant to the programmed chemistry. During or subsequent to entry, the present apparatus then displays and/or prints the programmed sequence to ensure accuracy, as well as permits the operator to rewrite the programmed sequence via CLEAR and ENTER functions.

The specific subroutines that are operator selectable are shown in Table 1 below and primarily consist of the addition of each of the individual bases as well as the addition of a number of combinations of the bases. It is to be recognized though that while only combinations of two bases are shown, additional combinations of 3 and 4 bases may also be programmed into the subroutine listing so as to provide the operator with still further flexibility. Also, should the operator desire to vary the chemistry, then it may be necessary to vary the subroutines so as to account for changes in the reagents/solvents, the sequence for adding same, the timing, etc.

TABLE 1

| BASE(s) | ENTRY |
|---|---|
| ADENINE (A) | GOSUB 100 |
| CYTOSINE (C) | GOSUB 200 |
| GUANINE (G) | GOSUB 300 |
| THYMINE (T) | GOSUB 400 |
| AC | GOSUB 210 |
| AG | GOSUB 220 |
| AT | GOSUB 230 |
| CG | GOSUB 240 |
| CT | GOSUB 250 |
| GT | GOSUB 260 |

With reference to Example 1 (below), an example of a typical sequence might be d(CACGACCCCT-CCACGT) and for which the operator enters the following program listing below. Upon entering the desired sequence, the operator directs the apparatus to go to the first step, execute, print and run. The apparatus in response thereto then begin the first cycle or first base addition by proceeding to an initial methylene chloride-isopropyl alcohol (IPA) wash and continues through a series of cycles during which each of the individual bases are added. Upon completing the end routine the apparatus then stops. During the performance of the routine though, the apparatus displays the total time elapsed as well as the time remaining within each of the individual cycles as they progress.

EXAMPLE 1:

| STEP | ENTRY | MEANING |
|---|---|---|
| 001 | GOSUB 200 | C |
| 002 | GOSUB 100 | A |
| 003 | GOSUB 200 | C |
| 004 | GOSUB 300 | G |
| 005 | GOSUB 100 | A |
| 006 | GOSUB 200 | C |
| 007 | GOSUB 200 | C |
| 008 | GOSUB 200 | C |
| 009 | GOSUB 200 | C |
| 010 | GOSUB 400 | T |
| 011 | GOSUB 200 | C |
| 012 | GOSUB 200 | C |
| 013 | GOSUB 100 | A |
| 014 | GOSUB 200 | C |
| 015 | GOSUB 300 | G |
| 016 | GOSUB 400 | T |
| 017 | GOSUB 990 | END ROUTINE |
| 018 | STOP | STOP |

Similarly if the operator desired to program a mixed probe, he/she would again list the individual subroutines, including the desired mixed bases. The apparatus upon detecting the mixed subroutines would then cause proportional amounts of each of the bases to be added to the reaction cell 14 at the specified cycle of the linking sequence. An example of a mixed probe sequence can be seen upon reference to Example 2 below.

EXAMPLE 2:d(AACTGGTATTACTGGGCG)
                A         C

| STEP | ENTRY | MEANING |
|---|---|---|
| 001 | GOSUB 100 | A |
| 002 | GOSUB 100 | A |
| 003 | GOSUB 200 | C |
| 004 | GOSUB 400 | T |
| 005 | GOSUB 220 | G + A |
| 006 | GOSUB 300 | G |
| 007 | GOSUB 400 | T |
| 008 | GOSUB 100 | T |
| 009 | GOSUB 400 | T |
| 010 | GOSUB 400 | T |
| 011 | GOSUB 100 | A |
| 012 | GOSUB 200 | C |
| 013 | GOSUB 250 | T + C |
| 014 | GOSUB 300 | G |
| 015 | GOSUB 300 | G |
| 016 | GOSUB 300 | G |
| 017 | GOSUB 200 | C |
| 018 | GOSUB 300 | G |
| 019 | GOSUB 990 | END ROUTINE |
| 020 | STOP | STOP |

Figure 7:
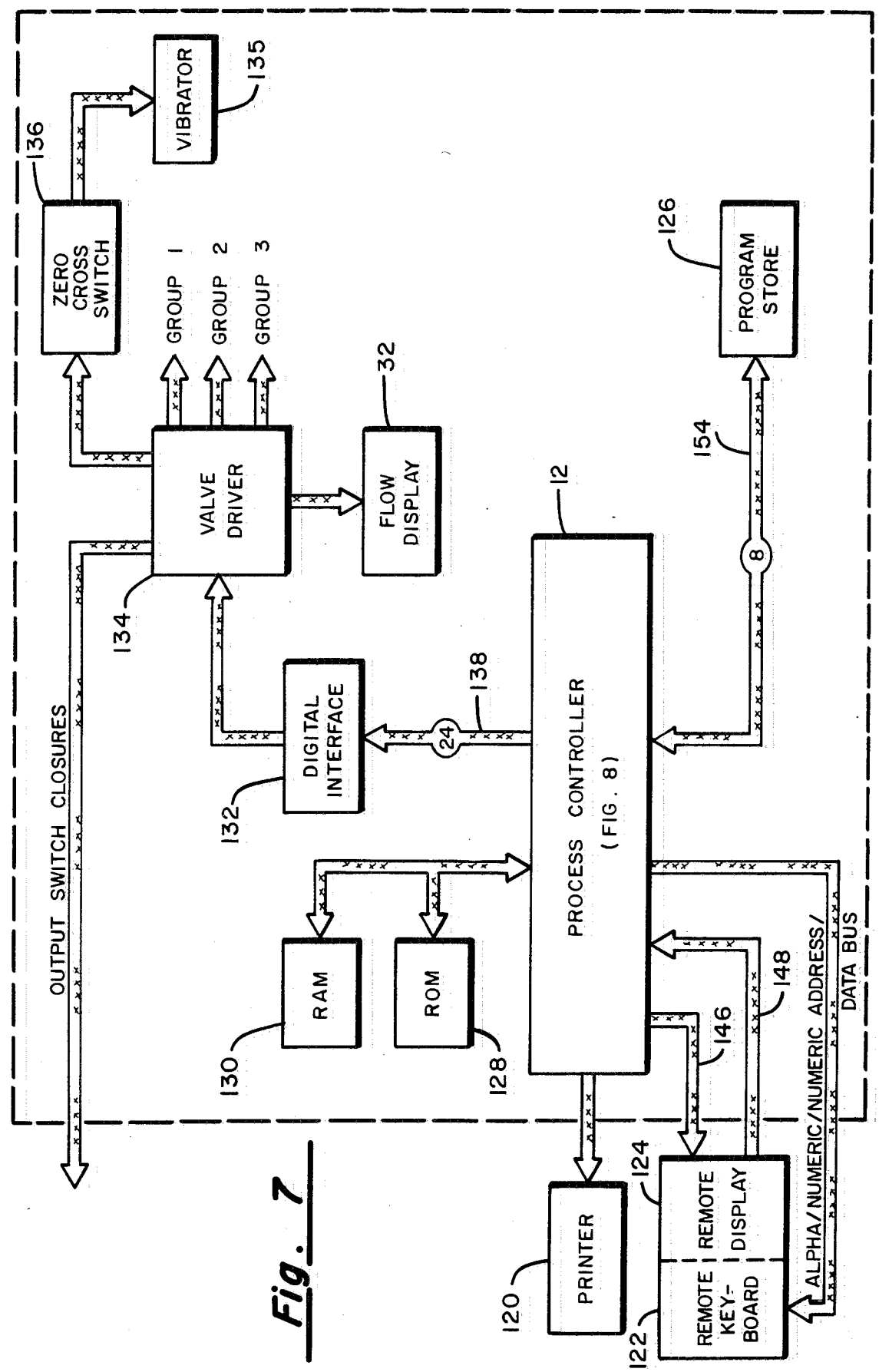
FIG. 7 shows a generalized schematic diagram of the control and communications circuitry.

With the above general programming operation in mind and recognizing that the steps of each base addition subroutine is peculiar to the selected chemistry, attention is now directed to FIG. 7, wherein a general block diagram is shown of the control circuitry for the present apparatus. Such circuitry is generally organized about the process controller 12 (shown in detail in FIG. 8). Peripheral to the controller 12 and associated therewith for facilitating communications are a printer 120, a remote keyboard 122 and a remote display 124. With respect to the programmed operation, a peripheral program store 126, and internal read only memory (ROM) 128 and random access memory (RAM) 130 are provided. With respect to the valve body selection control signals and the displaying thereof, a number of other functional elements are provided and which comprise digital interface 132, air pressure control valve driver 134, flow display 32, zero crossing switch 136, vibrator 135 and a plurality of controlled buses and grouped output ports from the valve driver 134.

Referring now to the various functional elements, the remote keyboard 122 and display 124 interact with the process controller 12 so as to permit the operator to enter subroutine sequences similar to the previous example and to view the data entered. Should errors occur during entry, these may be corrected and viewed so as to ensure their accuracy. During the actual processing, the display also serves the additional function of permitting the operator at any given time to visually determine which subroutine is being performed as well as determine the amount of time remaining for that given cycle and the total elapsed time for the sequence in process. A hard copy of the variously displayed data or process information is also available via the printer 120 and which for the preferred embodiment is coupled to the controller 12 at a 600 baud rate. Depending upon the capabilities of the process controller 12, further functional features, such as temperature monitoring, automatic test analysis etc. may be coupled via the processor 12 to the remote display 124 and provide the operator with a real time monitoring capability.

Operator entered data, such as the base nucleotide sequence and various operator programmable process parameters (e.g. time, etc.), upon entry are stored in RAM 130, where they are accessed at appropriate times by the controller 12 as it proceeds through the preprogrammed subroutines stored in the program store 126. For the present system, the program store 126 comprises a standard mini-cassette tape deck, which communicates with controller 12 at a 600 baud rate. It should thus be apparent that while the phosphotriester chemistry has presently been selected as an example any chemistry, any of the various other well known chemistries or for that matter operator initiated chemistries can be programmed into program store 126 in a similar fashion. Thus, the present apparatus is adaptable to all known chemistries or operator determined chemistries and operates in general purpose fashion, rather than in the special purpose fashion of heretofore known synthesizers.

ROM 128, like RAM 130, is addressable by the process controller 12 and acts to store addressable data, such as various ones of the 16 characters which may be displayed on the remote display 124 or the various control words that are used to selectively actuate the various valve bodies 104 during each cycle.

In this latter regard, as each cycle proceeds, the controller 12 outputs serial data via the address/data bus 138 to the digital interface unit 132. A typical data word is 24 bits wide and is comprised of three eight bit segments, since the present microprocessor is an 8 bit microprocessor. It is to be recognized though that various 16 or 32 bit microprocessors will also serve the present function, albeit with greater cost. As each data word is received by the interface 132, the data is latched into six latches of four bits each, prior to being coupled to the valve driver circuitry 134. At the valve driver, depending upon the handwiring of the various bit positions of the data, the data is broken into a number of fields which control various machine functions, depending upon which of the bits are enabled. In particular, the bit fields control the flow display 32 so as to appropriately turn the various back lights on and off, thereby indicating process status to the operator; provide a number of output switch closures, such as for peripheral test equipment; actuate the vibrator 135; and operate the various valve bodies and as well as control other cycle operations assigned to the group 1, 2 and 3 output ports, but which will be described in greater detail hereinafter.

Before addressing these latter functions, it is to be noted that the zero cross switch 136 essentially acts to monitor the vibrator-enabling control signals. At the same time it also monitors the AC power signal to the vibrator 135 in order to detect a zero crossing condition (i.e. the point at which the AC voltage signal is zero). Upon concurrently detecting a zero crossing condition and a vibrator enable signal, the zero cross switch 136 enables the vibrator 135. The zero cross switch 136 thus alleviates system noise and minimizes interference which might otherwise occur, since the present vibrator mechanism 135 is of an inductive type and which might otherwise possibly interject noise into the system if switched other than at a zero crossing.

With respect to the bit positions or fields for controlling the group 1, 2 and 3 output ports, attention is next directed to Table 2 below and wherein the specific valve and relay assignments for the present apparatus are shown. Thus, depending upon which of the three bit groups at the various ports are selected, various ones of the valve bodies 104 are enabled for appropriate amounts of time during each cycle. It is to be noted that the actual time is monitored by the controller 12 via its internal crystal oscillator and other various well known control circuitry that acts to divide-down the clock frequency and count the divided signals so as to provide the clock signals necessary to show total elapsed time as well as cycle time remaining.

TABLE 2

| I/O GROUP | PORT | FUNCTION |
| --- | --- | --- |
| VALVE AND RELAY ASSIGNMENTS | | |
| 1 | 1 | Zinc Bromide—IPA—$CH_2CL_2$ Valve |
| 1 | 2 | $CH_2CL_2$—IPA Valve |
| 1 | 3 | DMF Valve |
| 1 | 4 | THF Valve |
| 1 | 5 | Capping Reagent #1 |
| 1 | 6 | Capping Reagent #2 |
| 1 | 7 | Reagent Selection Valve |
| 1 | 8 | Pyridine Valve |
| 2 | 1 | Guanine in Pyridine Syringe/Valve |
| 2 | 2 | Cytosine in Pyridine Syringe/Valve |
| 2 | 3 | Adenine in Pyridine Syringe/Valve |
| 2 | 4 | Thymine in Pyridine Syringe/Valve |
| 2 | 5 | MSNT |
| 2 | 6 | $N_2$ Backflush/Solvent Reagent Valve |
| 2 | 7 | Waste-Collect Valve |
| 2 | 8 | Syringe Up/Syringe Down |
| 3 | 1 | Fraction Collector Advance |
| 3 | 2 | Not Used |
| 3 | 3 | Synthesis Cell Vibrator On/Off |
| 3 | 4 | Auxiliary Contact Closure |
| 3 | 5 | Cell Temperature Off |

Figures 8, 8A:
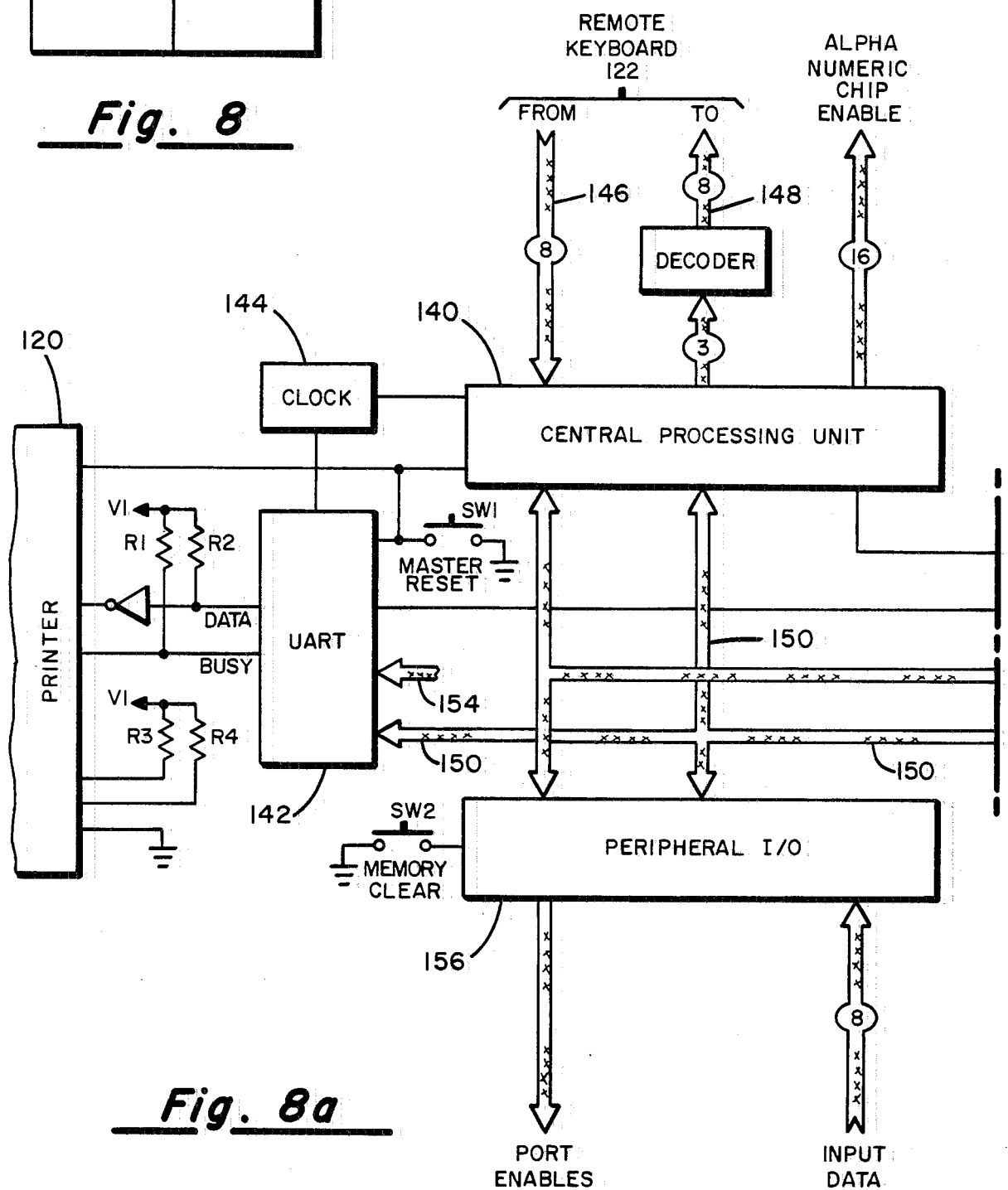
FIG. 8, comprised of FIGS. 8a and 8b, shows a detailed schematic of the process controller.
Figure 8B:
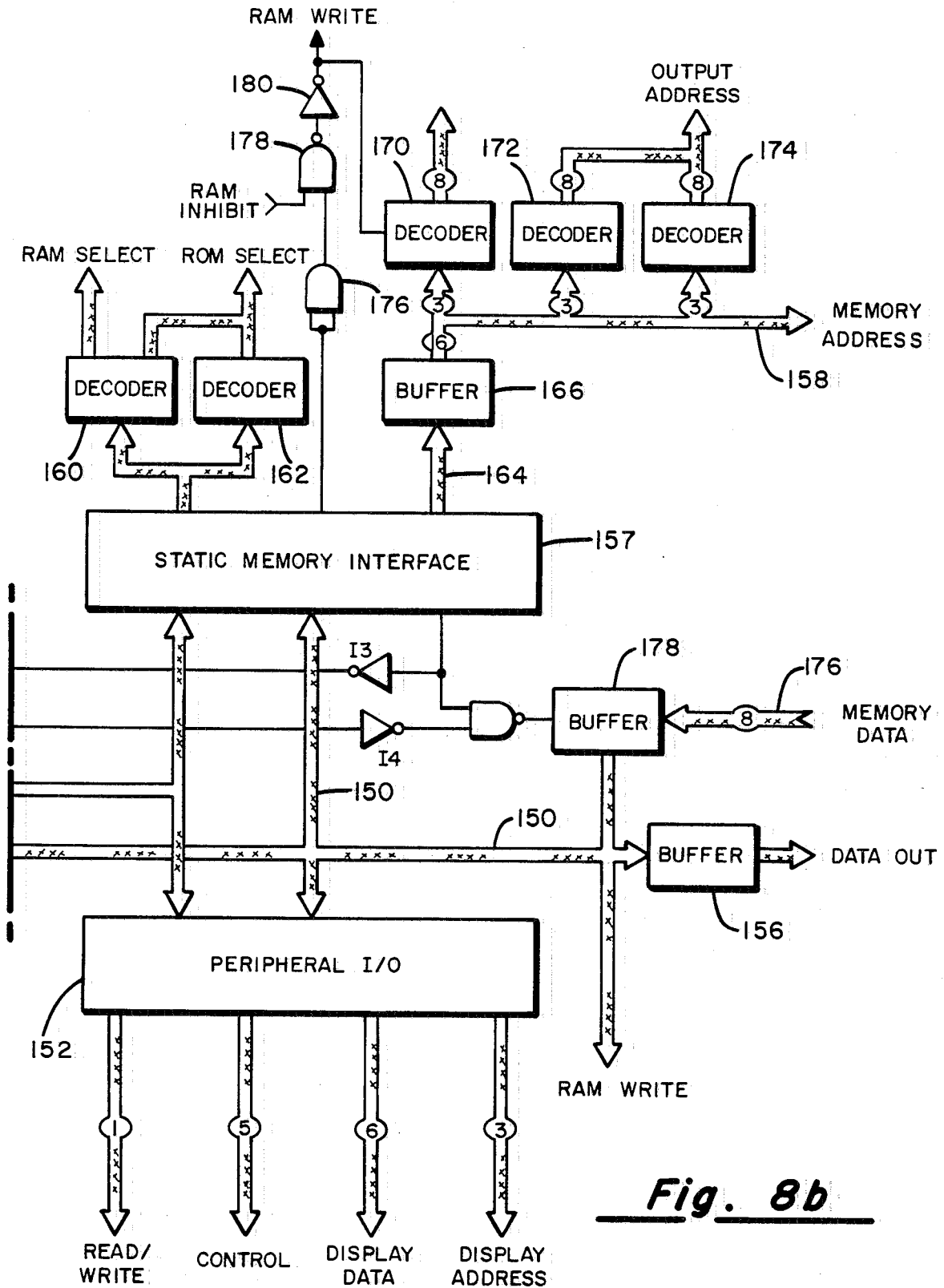

Referring now to FIG. 8, comprised of FIGS. 8a and 8b, a more detailed schematic diagram is shown of the process controller 12 and its manner of interfacing with the various peripheral circuitry previously described with respect to FIG. 7. Central to the process controller 12 is the central processing unit (CPU) 140 and which in the present embodiment is a Fairchild F8 microprocessor. The actual operation of the microprocessor will therefore not be discussed in detail, but if further information is required, attention is directed to various Fairchild product literature as it relates to the Model F8 mircoprocessor. Generally though and for the present apparatus, the microprocess serves to monitor and execute the operator programmed sequence with respect to the chemistry related subroutines stored in program store 126 (and which are written into RAM 140 via the CPU 140, peripheral I/O 152 and UART 142 upon powering up the present apparatus), while timing the various requisite operations.

As the CPU 140 performs its timing and data transfer functions, it communicates with the various associated peripheral circuitry via a number of interface units. In particular with respect to the printer 120, the CPU 140 is coupled to a universal asynchronous receiver/transmitter (UART) 142 that is appropriately biased so as to receive low level parallel data from the CPU 140 and couple it serially to the printer 120 at a 600 baud rate, as determined, by 2 the megahertz clock 144.

Similarly, the CPU 140 is coupled to the remote keyboard 122 via an 8 bit input bus 146 and 8 bit output bus 148. The keyboard 122, in turn, is configured as a switching matrix so as to produce an 8 bit character representative of each of its keys and which is received and decoded and by the CPU 140. Upon decoding the received data and assuming that the data is to be coupled to the remote display 124, the CPU 140 places the data along with various control and enable signals on data bus 150. The static memory interface (SMI) 157 in response to a position of the control signals establishes a write enable and the address location in the remote display 124 and after which the data is transmitted by buffer 156 to the corresponding addresses in remote display 124.

Similarly, during a read operation, when the CPU 140 is reading the preprogrammed subroutines from program store 126 and writing them into RAM 130, it transmits control signals via the I/O unit 152 to the tape player 126 so as to control the operation of the tape player 126 (i.e. stop/run; enable serial I/O; cassette present; fast forward/forward; and reverse). The preprogrammed data is then serially received by the UART 142 from but 154, translated by the UART 142 to parallel and transmitted via but 150 to RAM 130, all under the control of CPU 140. On the other hand and with reference to FIG. 7, if the CPU 140 desires to generate various switch closure enable signals, these are written via the data bus 150, under the control of the CPU 140, and SMI 157 to provide valve control through digital interface 132 to the valve driver 134. It is to be noted though that at present no input switch closure assignments have been established and therefore the I/O unit 156 serves future expansion.

Referring next to the circuitry associated with the CPU 140's interfacing with the ROM 128 and RAM 130, it is to be noted that appropriate address data is coupled to a static memory interface unit 157, where depending upon whether ROM 128 is to be read or RAM 130 is to be read or written, a portion of the address data is decoded via the ROM/RAM decoders 160 and 162 to establish which 1K of the 4K of RAM (130) or 12K of ROM (128) is to be selected. At the same time the remaining 16 bits of the address data are coupled via bus 164 to buffer 166 and from there to the memory address bus 158 and the associated decoders 170, 172 and 174. Under appropriate circumstances, the outputs of decoders 170, 172 and 174 are used to address the display and valve control functions and which at the same time obtain their control signals and from data bus 150 through buffer 156.

Otherwise, during the reading or writing of RAM 130 or ROM 128 and after the selection of the proper portion of memory, the address on memory address bus 158 is coupled to the selected memory where that address is read or written. If data is read from the selected address, it is received via input bus 176 and buffered via buffer 178 before being coupled to the CPU 140 by data bus 150. If on the other hand, data was written into the RAM 130, such as operator programmed data, it is conveyed via the data bus 150 to RAM 130 at the address determined in the above fashion.

With the earlier mentioned general operation and description of the electro-mechanical apparatus in mind, the particular DNA synthesis program used to perform the phosphotriester chemistry with the present apparatus will now be described. In this regards, attention will be directed from time to time to various tables and representative flow charss shown in FIGS. 9 and 10 for selected portions of the program. Generally though, the present example synthesis program can be seen upon reference to the summary thereof in Table 3 (below) and wherein the various subroutine functions along with their assigned steps are shown. For purposes of description, it is to be noted that this listing can be broken down into those functions related to the operator programming of a desired DNA coupling sequence (001–099); functions for selecting various ones or combinations of the individual bases; functions for adding the selected bases or combinations to the reaction cell with appropriate preparation and washout steps; functions for performing the washing of the reaction cell; and post addition functions for ensuring that the apparatus is ready for the next base addition.

TABLE 3
Phosphotriester Method
DNA SYNTHESIS PROGRAM SUMMARY

| STEPS | ROUTINE |
|---|---|
| 001–099 | Reserved for entry of DNA coupling sequence |
| 100–104 | Add Adenine |
| 200–204 | Add Cytosine |
| 210–214 | Couple A & C (Mixed Probe) |
| 220–224 | Couple A & G (Mixed Probe) |
| 230–234 | Couple A & T (Mixed Probe) |
| 240–244 | Couple C & G (Mixed Probe) |
| 250–254 | Couple C & T (Mixed Probe) |
| 260–264 | Couple G & T (Mixed Probe) |
| 300–304 | Add Guanine |
| 400–404 | Add Thymine |
| 500–505 | Base addition preparation |
| 510–521 | $CH_2Cl_2$ IPA Wash |
| 525–547 | Zinc Bromide ($ZnBr_2$) Wash |
| 550–561 | Dimethyl Formadine Wash |
| 565–575 | Pyridine Wash |
| 580–594 | Final Wash |
| 600–616 | Adding and Coupling Adenine |
| 620–636 | Adding and Coupling Cytosine |
| 640–656 | Adding and Coupling Guanine |
| 660–676 | Adding and Coupling Thymine |
| 680–698 | Mixed AC Synthesis Addition |
| 700–718 | Mixed AG Synthesis Addition |
| 720–738 | Mixed AT Synthesis Addition |
| 740–758 | Mixed CG Synthesis Addition |
| 760–778 | Mixed CT Synthesis Addition |
| 780–798 | Mixed GT Synthesis Addition |
| 950–957 | Syringe Refresh |
| 960–964 | Post reaction Pyridine Wash/$N_2$ Blowdown |
| 970–981 | Capping Routine |
| 990–993 | End Routine |

With the above simplification in mind, attention is directed to Table 4 wherein a detailed listing is shown of the functions performed by the various subroutines. From Table 4, it is to be noted that steps 100 to 104, 200 to 204, 300 to 304, 400 to 404, 210 to 214, 220 to 224, 230 to 234, 240 to 244, 250 to 254 and 260 to 264 essentially rely upon various others of the subroutines for selecting one or more bases, mixing the bases together for a mixed probe, coupling the bases to the nucleotide seeded resin, washing the reaction cell and capping the desired ends of the nucleotide preparatory to the next base addition. Prior to a base addition though, numerous wash and dry operations are performed and which are listed in steps 500 to 594. During the washing steps, the apparatus operates to successively wash the reaction cell with methylene chloride, the zinc bromide detritylating reagent, a DMF wash, a pyridine wash and a THF wash/dry operation. Also, it is to be noted that various of the washing steps are performed more than one time to ensure the removal of all previously admitted chemicals to the reaction cell 14 and thereby proper coupling, upon adding the next volume of base.

Upon reference to the various coupling steps, it is to be noted that they each call upon a subroutine for adding a single base or a mixed base (comprised of two or more bases). Such single base additions subroutines are set forth in steps 600 to 616, 620 to 636, 640 to 656 and 660 to 676. The mixed base additions, on the other hand, are set forth in steps 700 to 718, 720 to 738, 740 to 758, 760 to 778 and 780 to 798.

Subsequent to each base addition, various post addition steps are performed and which refresh or refill the syringes, perform a pyridine wash and nitrogen blow down of the reaction cell, capping the ends of the nucleotide sequences prior to the addition of the next base and an END subroutine which turns off the vibrator motor, cell temperature controller 34 and resets the elapsed time counter. It is to be noted though that the END routine is used only at the end of the programmed nucleotide sequence, just prior to stopping.

For more information with respect to each of the subroutine listings and the various steps performed therein, attention is directed to Table 4 (below) and the rather comprehensive individual subroutine listings. Upon reference thereto, it is to be noted that various ones of the subroutines also provide for operator intervention, whereby the operator may program additional cycles, time variation or volume variation of the various chemicals and reactions for those subroutines. In this way, the operator is able to vary the synthesis reactions as desired. Thus, within the given chemistry, the operator has a wide latitude of discretion via the present general purpose synthesizer. It is again to be recalled too that this latitude is further increased to various other chemistries by merely substituting appropriate programs therefore into the program store 126 and accessing such chemistries in the same fashion as for the present chemistry.

TABLE 4

SYNTHESIS SUBROUTINE LISTING
BASE COUPLING ROUTINES:

| STEP | COMMAND | ACTION/MEANING |
|---|---|---|
| COUPLE ADENINE (A) | | |
| 100 | GO SUBRTN 500 | Base Addition Preparation |
| 101 | GO SUBRTN 600 | Couple A |
| 102 | GO SUBRTN 960 | Pyridine washout |
| 103 | GO SUBRTN 970 | Cap Ends |
| 104 | RETURN 0 | Return |
| COUPLE CYTOSINE (C) | | |
| 200 | GO SUBRTN 500 | Base Addition Preparation |
| 201 | GO SUBRTN 620 | Couple C |
| 202 | GO SUBRTN 960 | Pyridine washout |
| 203 | GO SUBRTN 970 | Cap Ends |
| 204 | RETURN 0 | Return |
| COUPLE GUANINE (G) | | |
| 300 | GO SUBRTN 500 | Base Addition Preparation |
| 301 | GO SUBRTN 640 | Couple G |
| 302 | GO SUBRTN 960 | Pyridine washout |
| 303 | GO SUBRTN 970 | Cap Ends |
| 304 | RETURN 0 | Return |
| COUPLE THYMINE (T) | | |
| 400 | GO SUBRTN 500 | Base Addition Preparation |
| 401 | GO SUBRTN 660 | Couple T |
| 402 | GO SUBRTN 960 | Pyridine washout |
| 403 | GO SUBRTN 970 | Cap Ends |
| 404 | RETURN 0 | Return |
| COUPLE A & C AT SAME POSITION (MIXED PROBE) | | |
| 210 | GO SUBRTN 500 | Base Addition Preparation |
| 211 | GO SUBRTN 680 | Add mixed A & C |
| 212 | GO SUBRTN 960 | Pyridine washout |
| 213 | GO SUBRTN 970 | Cap Ends |
| 214 | RETURN 0 | Return 0 |
| COUPLE A & G AT SAME POSITION (MIXED PROBE) | | |
| 220 | GO SUBRTN 500 | Base Addition Preparation |
| 221 | GO SUBRTN 700 | Add mixed A & G |
| 222 | GO SUBRTN 960 | Pyridine washout |
| 223 | GO SUBRTN 970 | Cap Ends |
| 224 | RETURN 0 | Return 0 |
| COUPLE A & T AT SAME POSITION (MIXED PROBE) | | |
| 230 | GO SUBRTN 500 | Base Addition Preparation |
| 231 | GO SUBRTN 720 | Add mixed A & T |
| 232 | GO SUBRTN 960 | Pyridine washout |
| 233 | GO SUBRTN 970 | Cap Ends |
| 234 | RETURN 0 | Return 0 |
| COUPLE C & G AT SAME POSITION (MIXED PROBE) | | |
| 240 | GO SUBRTN 500 | Base Addition Preparation |
| 241 | GO SUBRTN 740 | Add mixed C & G |
| 242 | GO SUBRTN 960 | Pyridine washout |

TABLE 4-continued

SYNTHESIS SUBROUTINE LISTING
BASE COUPLING ROUTINES:

| STEP | COMMAND | ACTION/MEANING |
|---|---|---|
| 243 | GO SUBRTN 970 | Cap Ends |
| 244 | RETURN 0 | Return 0 |
| COUPLE C & T AT SAME POSITION (MIXED PROBE) | | |
| 250 | GO SUBRTN 500 | Base Addition Preparation |
| 251 | GO SUBRTN 760 | Add mixed C & T |
| 252 | GO SUBRTN 960 | Pyridine washout |
| 253 | GO SUBRTN 970 | Cap Ends |
| 254 | RETURN 0 | Return 0 |
| COUPLE G & T AT SAME POSITION (MIXED PROBE) | | |
| 260 | GO SUBRTN 500 | Base Addition Preparation |
| 261 | GO SUBRTN 780 | Add mixed G & T |
| 262 | GO SUBRTN 960 | Pyridine washout |
| 263 | GO SUBRTN 970 | Cap Ends |
| 264 | RETURN 0 | Return 0 |

BASE ADDITION PREPARATION ROUTINES; PHOSPHOTRIESTER METHOD

This subroutine lines up the subroutines necessary to complete all the steps prior to the addition of the base(s). It makes use of the multiple subroutine capability of the controller and eliminates the necessity of writing all five GO SUBRTN statements in each base coupling sequence.

| STEP | COMMAND | ACTION/MEANING |
|---|---|---|
| 500 | GO SUBRTN 510 | Methylene chloride - IPA wash (see Step 510) |
| 501 | GO SUBRTN 525 | Zinc bromide (detriylation) step (see Step 525) |
| 502 | GO SUBRTN 550 | DMF wash (see Step 550) |
| 503 | GO SUBRTN 565 | Pyridine wash (see Step 565) |
| 504 | GO SUBRTN 580 | THF wash/dry (see Step 580) |
| 505 | RETURN 0 | Return from subroutine |

$CH_2Cl_2$-IPA(85:15)WASH

This subroutine prewashes the resin with methylene chloride isopropyl alcohol; removes any remaining capping reagent solvents; and preswells the resin for the deblocking step. The subroutine contains three separate wash and nitrogen backflush cycles.

| STEP | COMMAND | PURPOSE |
|---|---|---|
| 510 | SET LP CNT20003 | Do the wash sequence (steps 511–516) 3 times, using counter 2. |
| 511 | SET CLOSE 12 | Turn on valve 12 for $MeCl_2$—IPA wash. |
| 512 | SET CLOSE 17 | Open valve 17 so $MeCl_2$—IPA can flow to cell. |
| 513 | INTVL TM 001.00 | Allow 1 min. for solvent flow (adjustable). |
| 514 | SET CLOSE 26 | Shuts off all solvent flow to cell, $N_2$ backflush cell. |
| 515 | INTVL TM 000.20 | $N_2$ backflush for .20 min. (adjustable). |
| 516 | SET OPEN 26 | $N_2$ backflush OFF, resume solvent flow to cell. |
| 517 | INC LP CNT 2519 | Add 1 to total in counter 2, when total reaches number set in Step 100 go to 519, otherwise go to 518. |
| 518 | GO TO 511 | Till loop counter 2 = total set in step 510, go back to 511 and repeat sequence. |
| 519 | SET OPEN 12 | Turn off $MeCl_2$—IPA valve. |
| 520 | SET OPEN 17 | Turn off reagent selection valve. |
| 521 | RETURN 0 | Return to main program from subroutine. |

PROGRAMMABLE

| PARAMETERS: | STEP | ENTRY |
|---|---|---|
| Change # of total cycles | 510 | Set LP CNT 2XXXX<br>XXXX = Count (total cycles)<br>Increase or decrease pressure on supply vessel, OR |
| Change volume of solvent per flush cycle on supply vessel, | 513 | INTVL TM TTT.TT-increase TTT.TT (time) for more solvent |

ZINC BROMIDE(ZnBr$_2$)DETRITYLATION (Other detritylating reagents may be substituted)

This subroutine contains several control sequences so as to control the fraction collector advance, the waste-collect valve and cell vibrator. The sequence flushes the cell twice with the zinc bromide solution, collecting each flush in an individual test tube for later spectrophotometric analysis.
1. Advance fraction collector
2. Waste valve to collect position
3. Select reagents and turn on vibrator
4. Flow zinc bromide 2 min.
5. Stop flow for 2 min. ZnBr$_2$ Reaction
6. Nitrogen backflush cell to test tube
7. Two times through MeCl$_2$-IPA wash subroutine
8. Advance fraction collector
9. Do steps 4–7 again
10. Return to main program.

| STEP | COMMAND | PURPOSE |
|---|---|---|
| 525 | SET CLOSE 31 | Advance Fraction Collector |
| 526 | INTVL TM 0000.01 | Hold Advance Relay closed 0.01 min. |
| 527 | SET OPEN 31 | Stop fraction collector advance |
| 528 | SET CLOSE 27 | Waste valve to collect position |
| 529 | SET LP CNT 10002 | Do steps 530–545 two times |
| 530 | SET CLOSE 17 | Select the reagents to the cell |
| 531 | SET CLOSE 33 | Turn on the vibrator |
| 532 | SET CLOSE 11 | Turn on ZnBr$_2$ flor to synthesis cell |
| 533 | INTVL TM 002.00 | All ZnBr$_2$ to flow thru cell 2.00 min. |
| 534 | SET OPEN 11 | Stop the flow through the cell |
| 535 | INTVL TM 002.00 | Hold ZnBr$_2$ Solution in cell for 2 min. |
| 536 | SET CLOSE 26 | Start N$_2$ backflush of cell |
| 537 | INTVL TM 000.15 | Backflush cell with N$_2$ for 0.15 min. |
| 538 | SET OPEN 26 | Stop N$_2$ backflush, ZnBr$_2$ residue still in cell |
| 539 | SET LP CNT 20002 | Set up IPA—CH$_2$Cl$_2$ wash for 2 times |
| 540 | GO SUBRTN 511 | Go through IPA—CH$_2$Cl$_2$ wash 2 times, remove ZnBr$_2$. |
| 541 | INC LP CNT 1546 | Add 1 to total in counter 1, when total reaches number set in step 529, go to 546, else go to 542. |
| 542 | SET CLOSE 31 | Advance fraction collector |
| 543 | INTVL TM 000.01 | Hold advance relay closed 0.01 min. |
| 544 | SET OPEN 31 | Stop fraction collector advance |
| 545 | GO TO 530 | Till loop count 1 = set count (step 529) go back to 530, repeat. |
| 546 | SET OPEN 27 | Set waste valve to position |
| 547 | RETURN 0 | Retun from subroutine |

| PROGRAMMABLE PARAMETER: | STEP | ENTRY |
|---|---|---|
| Longer contact to advance | 526 | INTVL TM (TTT.TT) |
| fraction collector Time = TTT.TT | 543 | |
| More times through ZnBr$_2$ wash (or less) XXXX = Count | 529 | SET LP CNT (1XXXX) |
| More CH$_2$Cl$_2$—IPA washes Count = XXXX | 539 | SET LP CNT (2XXXX) |
| More static time for ZnBr$_2$ in cell Time = TTT.TT | 535 | INTVL TM (TTT.TT) |
| More N$_2$ backflush time for ZnBr$_2$ Time = TTT.TT | 537 | INTVL TM (TTT.TT) |

DIMETHYL FORMAMIDE(DMF)WASH

This wash removes residual methylene chloride and IPA from the deblocking step. It involves 3 separate washes of the resin and oligonucleotide chain after the deblocking with 3 nitrogen blowdowns of the cell.
1. Wash 1 minute with DMF (approximately 3.0 ml)
2. Nitrogen backflush
3. Repeat 1 & 2 two more times

| STEP | COMMAND | PURPOSE |
|---|---|---|
| 550 | SET LP CNT 30003 | Do steps 55–557 three times |
| 551 | SET CLOSE 17 | Select reagents |
| 552 | SET CLOSE 13 | Select DMF |
| 553 | INTVL TM 001.00 | Allow DMF to flow 1.00 min. |
| 554 | SET CLOSE 26 | N$_2$ backflush (stops DMF flow) |
| 555 | INTVL TM 000.50 | Allow N$_2$ .5 min. flow |
| 556 | SET OPEN 26 | Turn off N$_2$ backflush - DMF begins flow again. |
| 557 | INC LP CNT 3559 | Add 1 to counter 3. When = to count set in 550 go to 559, otherwise go to 558. |
| 558 | GO TO 551 | REPEAT |
| 559 | SET OPEN 17 | Select Syringes |
| 560 | SET OPEN 13 | Turn off DMF |
| 561 | RETURN 0 | Return from subroutine |

| PROGRAMMABLE PARAMETER: | STEP | ENTRY |
|---|---|---|
| More (or fewer) times DMF wash count = XXXX | 550 | SET LP CNT 3XXXX |
| More DMF Volume (increase pressure) Increase time TIME = TTT.TT | 553 | INTVL TM TTT.TT |
| Shorter (or longer) N$_2$ blowdown Inc/Dec TIME = TTT.TT | 555 | INTVL TM TTT.TT |

PYRIDINE WASH

Pyridine is used to watch out the DMF from the previous step.
1. Allow pyridine to flow 1.00 min. (3.0 ml)
2. Blow pyridine out of cell
3. Repeat one time

| STEP | COMMAND | PURPOSE |
|---|---|---|
| 565 | SET LP CNT 50002 | Use loop counter 5 and set for 2 times through loop to step 574 |
| 566 | SET OPEN 17 | Select syringes and Pyridine |
| 567 | SET CLOSE 18 | Turn on pyridine flow |
| 568 | INTVL TM 001.00 | Allow to flow 1.0 min. |
| 569 | SET OPEN 18 | Turn off Pyridine |
| 570 | SET CLOSE 26 | Turn on N$_2$ Backflush |
| 571 | INTVL TM 000.50 | Backflush 30 seconds |
| 572 | SET OPEN 26 | Turn off N$_2$ Backflush |
| 573 | INC LP CNT 5575 | Add 1 to counter 5. When = to count set in 565, go to 575, otherwise 574 |
| 574 | GO TO 566 | Repeat |
| 575 | RETURN 0 | Return from subroutine |

| PROGRAMMABLE PARAMETERS: | STEP | COMMAND |
|---|---|---|

| | | |
|---|---|---|
| More time/or less/thru loop count = XXXX | 565 | SET LP CNT (5XXXX) |
| More Pyridine per wash (increase pressure or more time)-TTT.TT | 568 | INTVL TM (TTT.TT) |
| More $N_2$ Backflush Time /or less/ Time = TTT.TT | 571 | |

FINAL WASH

This routine is the last wash prior to the addition of the bases. This step removes the pyridine and uses THF as a highly volatile solvent and is easily removed from the resin by a dry nitrogen blowdown and which also effectively allows the resin to be thoroughly dried prior to introduction of the base and MSNT coupling reagent. The reagent and base then well the resin such that the base penetrates all the resin pores available.

1. Flow pyridine (3 ml) 1.0 min. (1st time-3 ml may not make it).
2. $N_2$ blowdown.
3. Repeat 3 times.
4. Three minute blow dry with $N_2$.

| STEP | COMMAND | PURPOSE |
|---|---|---|
| 580 | SET LP CNT 40003 | Set up counter 4 for 3 times through loop to step 588 |
| 581 | SET CLOSE 17 | Set reagents |
| 582 | SET CLOSE 14 | Select THF |
| 583 | INTVL TM 1.00 | Flow THF for 1 min. |
| 584 | SET CLOSE 26 | Turn on $N_2$ Backflush (turns off THF) |
| 585 | INTVL TM 000.25 | Backflush 15 seconds with $N_2$ |
| 586 | Set OPEN 26 | Turn OFF $N_2$ Backflush (turns of THF) |
| 587 | INC LP CNT 4589 | Add 1 to counter 4, when = to count set in 580, Go To 589, otherwise 588 |
| 588 | GO TO 581 | REPEAT |
| 589 | SET OPEN 17 | Turn off Reagents |
| 590 | SET OPEN 14 | Turn off THF |

| STEP | COMMAND | PURPOSE |
|---|---|---|
| 591 | SET CLOSE 26 | Turn on $N_2$ Backflush again |
| 592 | INTVL TM 003.00 | Backflush for 3 min. (or till dry) |
| 593 | SET OPEN 26 | Turn off Backflush |
| 594 | RETURN 0 | Return from subroutine |

BASE DISPENSING ROUTINES

The following routines are used to dispense the bases and the MSNT in equal volumes into the synthesis cell. Since the mechanism loads all the syringes and dispenses the contents of all the syringes each time a base is needed, the controller selects which syringes will deliver to the cell and which will deliver back to the supply vial. Thus, any combination of syringes may be selected at random under program control to synthesize any possible strand of DNA.

The subroutines that follow depend on the proper arrangement of the base vials on the synthesizer. The vial-syringe assignments used for the present program are as follows:

| Base Vial | Valve No. |
|---|---|
| Guanine | V-21 |
| Cytosine | V-22 |
| Adenine | V-23 |
| Thymine | V-24 |
| MSNT | V-25 |

Each subroutine follows the following sequence:
1. Pump syringe once and fill
2. Select MSNT and Valve(s) to deliver to cell
3. Deliver base(s) and MSNT
4. Refill syringes
5. Discharge 1 syringe load of MSNT to push dead volume to cell
6. Add 1 to counter 9. Nine shows the chain length
7. Wait 25 minutes for reaction to complete
8. Return

ADD ADENINE

| STEP | COMMAND | PURPOSE |
|---|---|---|
| 600 | GO SUBRTN 950 | Pump syringes once and fill |
| 601 | SET CLOSE 25 | Select MSNT to deliver to cell |
| 602 | SET CLOSE 23 | Select Adenine to deliver to cell |
| 603 | SET OPEN 28 | Drive syringe up |
| 604 | INTVL TM 000.05 | Deliver MSNT 7 Adenine to cell |
| 605 | SET OPEN 25 | Select MSNT syringe to reload from vial |
| 606 | SET OPEN 23 | Select Adenine syringe to reload from vial |
| 607 | SET CLOSE 28 | Draw bases-MSNT from vials to fill syringes |
| 608 | INTVL TM 000.05 | Allow three seconds of fill |
| 609 | SET CLOSE 25 | Select MSNT to push to cell a dead volume |
| 610 | SET OPEN 28 | Deliver MSNT to cell |
| 611 | INTVL TM 000.05 | Allow three seconds to deliver |
| 612 | SET OPEN 25 | MSNT to refill position |
| 613 | INC LP CNT 9999 | Add 1 to counter 9, "dummy-go-to" of 999 |
| 614 | DISP LT CNT 9 | Counter 9 now shows total couplings completed |
| 615 | INTVL TM 025.00 | Wait 25 mins. for reaction to occur |
| 616 | RETURN 0 | Return from subroutine |

| PROGRAMMABLE PARAMETERS: | STEP | ENTRY |
|---|---|---|
| Syringes need more time to load/deliver 608 | 604 | INTVL TM (TTT.TT) |
| | 611 | |
| More/less reaction time needed. Time = TTT.TT | | INTVL TM (TTT.TT) |

ADD CYTOSINE

| STEP | COMMAND | PURPOSE |
|---|---|---|

-continued

| 620 | GO SUBRTN 950 | Pump syringes once and fill |
|---|---|---|
| 621 | SET CLOSE 25 | Select MSNT to deliver to cell |
| 622 | SET CLOSE 22 | Select Cytosine to deliver to cell |
| 623 | SET OPEN 28 | Drive syringe up |
| 624 | INTVL TM 000.05 | Deliver MSNT & Cytosine to cell |
| 625 | SET OPEN 25 | Select MSNT syringe to reload from vial |
| 626 | SET OPEN 22 | Select Cytosine syringe to reload from vial |
| 627 | SET CLOSE 28 | Draw bases-MSNT from vials to fill syringes |
| 628 | INTVL TM 000.05 | Allow three seconds to deliver |
| 629 | SET CLOSE 25 | Select MSNT to push to cell dead volume |
| 630 | SET OPEN 28 | Deliver MSNT to cell |
| 631 | INTVL TM 000.05 | Allow three seconds to deliver |
| 632 | SET OPEN 25 | MSNT to refill position |
| 633 | INC LP CNT 9999 | Add to 1 counter 9, "dummy go-to" 999 |
| 634 | DISP LP CNT 9 | Counter 9 now shows total couplings completed |
| 635 | INTVL TM 025.00 | Wait 25 mins. for reaction to occur |
| 636 | RETURN 0 | Return froM subroutine |

| PROGRAMMABLE PARAMETERS: | STEP | ENTRY |
|---|---|---|
| Syringes need more time to load/dever 628 | 624 | INTVL TM (TTT.TT) |
|  | 631 |  |
| More/less reaction time needed. TiME = TTT.TT | 635 | INTVL TM (TTT.TT) |

ADD GUANINE

| STEP | COMMAND | PURPOSE |
|---|---|---|
| 640 | GO SUBTRN 950 | Pump syringes once and fill |
| 641 | SET CLOSE 25 | Select MSNT to deliver to cell |
| 642 | SET CLOSE 21 | Select Guanine to deliver to cell |
| 643 | SET OPEN 28 | Drive syringe up |
| 644 | INTVL TM 000.05 | Deliver MSNT & Guanine to cell |
| 645 | SET OPEN 25 | Select MSNT syringe to reload from vial |
| 646 | SET OPEN 21 | Select Guanine syringe to reoad from vial |
| 647 | SET CLOSE 28 | Draw bases-MSNT from vials to fill syringes |
| 648 | INTVL TM 000.05 | Allow three seconds to fill |
| 649 | SET CLOSE 25 | Select MSNT to push to cell a dead volume |
| 650 | SET OPEN 28 | Deliver MSNT to cell |
| 651 | INTVL TM 000.05 | Allow three seconds to deliver |
| 652 | SET OPEN 25 | MNST to refill position |
| 653 | INC LP CNT 999 | Add 1 to counter 9, "dummy-go-to" of |
| 654 | DISP LT CNT 9 | Counter 9 now shows total couplings completed |
| 655 | INVLT TM 025.00 | Wait 25 min's. for reaction to occur |
| 656 | RETURN 0 | Return from subroutine |

| PROGRAMMABLE PARAMETER: | STEP | ENTRY |
|---|---|---|
| Syringes need more time to load/deliver | 644 | INTVL TM (TTT.TT) |
|  | 648 |  |
|  | 651 |  |
| More/less reaction time needed. Time = TTT.TT | 655 | INTVL TM (TTT.TT) |

ADD THYMINE

| STEP | COMMAND | PURPOSE |
|---|---|---|
| 660 | GO SUBRTN 950 | Pump syringes once and fill |
| 661 | SET CLOSE 25 | Select MSNT to deliver to cell |
| 662 | SET CLOSE 24 | Select Thymine to deliver to cell |
| 663 | SET OPEN 28 | Drive syringe up |
| 664 | INTVL TM 000.05 | Deliver MSNT & Thymine to cell |
| 665 | SET OPEN 25 | Select MSNT syringe to relaod from vial |
| 666 | SET OPEN 24 | Select Thymine syringe to reload from vial |
| 667 | SET CLOSE 28 | Draw bases-MSNT from vials to fill syringes |
| 668 | INTVL TM 000.05 | Allow three seconds to fill |
| 669 | SET CLOSE 25 | Select MSNT to push to cell all dead volume |
| 670 | SET OPEN 28 | Deliver MSNT to cell |
| 671 | INTVL TM 000.05 | Allow three seconds to deliver |
| 672 | SET OPEN 25 | MSNT to refill position |
| 673 | INC LP CBT 9999 | Add 1 to counter 9, "dummy-go-to" 999 |
| 674 | DISP LP CNT 9 | Counter 9 now shows total couplings completed |
| 675 | INTVL TM 025.00 | Wait 25 mins. for reaction to occur |
| 676 | RETURN 0 | Return from subroutine |

| PROGRAMMABLE PARAMETERS: | STEP | ENTRY |
|---|---|---|
| Syringes need more time to load/deliver | 664 | INTVL TM (TTT.TT) |
|  | 663 |  |
|  | 671 |  |
| More/less reaction time needed. TIME = TTT.TT | 675 | INTVL TM (TTT.TT) |

MIXED PROBE (Two Base) SYNTHESIS ROUTINES

The following subroutines are used to synthesize mixed probes with two bases at a single position. Since the concentration of each individual base falls from 0.1M to 0.667M, a longer time may be necessary for reaction completion. Note that the last (25 min.) time may be changed to accommodate the longer reaction.

ADD AC

| STEP | COMMAND | PURPOSE |
|---|---|---|
| 680 | GO SUBRTN 950 | Charge syringes |
| 681 | SET CLOSE 25 | Select MSNT to cell |
| 682 | SET CLOSE 23 | Select Adenine to cell |
| 683 | SET CLOSE 22 | Select Cytosine to cell |
| 684 | SET OPEN 28 | Drive syringe up |
| 685 | INTVL TM 000.05 | Deliver MSNT, Adenine & Cytosine to synthesis cell |
| 686 | SET OPEN 25 | MSNT syringe to vial |
| 687 | SET OPEN 23 | Adenine syringe to vial |
| 688 | SET OPEN 22 | Cytosine syringe to vial |
| 689 | SET CLOSE 28 | Drive syringe down to refill |
| 690 | INTVL TM 000.05 | Refill all syringes |
| 691 | SET CLOSE 25 | Select MSNT to deliver to cell |
| 692 | SET OPEN 28 | Drive syringes up |
| 693 | INTVL TM 000.05 | Deliver MSNT to cell and clear dead volume |
| 694 | SET OPEN 25 | MSNT syringes selected to vial |
| 695 | INC LP CNT 9999 | Add 1 to loop counter 9 |
| 696 | DISP LT CNT 9 | Count in 9 now = total # of couplings |
| 697 | INTVL TM 025.00 | 25 min. reaction time (may need altering) |
| 698 | RETURN 0 | Return from subroutine |

| PROGRAMMABLE PARAMETERS: | STEP | ENTRY |
|---|---|---|
| More syringes fill/discharge time | 685 | INTVL TM (TTT.TT) |
|  | 690 |  |
|  | 693 |  |
| Longer reaction time. Time = TTT.TT | 697 | INTVL TM (TTT.TT) |

ADD A&G

| STEP | COMMAND | PROGRAM |
|---|---|---|
| 700 | GO SUBRTN 950 | Charge syringes |
| 701 | SET CLOSE 25 | Select MSNT to cell |
| 702 | SET CLOSE 23 | Select Adenine to cell |
| 703 | SET CLOSE 21 | Select Guanine to cell |
| 704 | SET OPEN 28 | Drive syringe up |
| 705 | INTVL TM 000.05 | Deliver MSNT, Adenine & Guanine to synthesic cell |
| 706 | SET OPEN 25 | Select MSNT from vial |
| 707 | SET OPEM 23 | Select Adenine from vial |
| 708 | SET OPEN 21 | Select Guanine from vial |
| 709 | SET CLOSE 28 | Refill syringes from vials |
| 710 | INTVL TM 000.05 | Allow 3 secs. for refill |
| 711 | SET CLOSE 25 | Select MSNT for push to cell to clear dead volume |
| 712 | SET OPEN 28 | Drive syringe up |
| 713 | INTVL TM 000.05 | Allow three seconds to deliver MSNT |
| 714 | SET OPEN 25 | Select MSNT vial |
| 715 | INC LP CNT 9999 | Add to counter 9. Count = # of steps done in sequence. |
| 716 | DISP LP CNT 9 | Display # of steps in the sequence completed |
| 717 | INTVL TM 025.00 | Wait 25.00 minutes for reaction (may need altering) |
| 718 | RETURN 0 | Return from subroutine |

| PROGRAMMABLE PARAMETERS: | STEP | ENTRY |
|---|---|---|
| More syringe fill/dischare time | 705 | INTVL TM (TTT.TT) |
|  | 710 |  |
|  | 713 |  |
| Longer reaction time. Time = TTT.TT | 717 | INTVL TM (TTT.TT) |

ADD A&T

| STEP | COMMAND | PURPOSE |
|---|---|---|
| 720 | GO SUBRTN 950 | Charge syringes |
| 721 | SET CLOSE 25 | Select MSNT to cell |
| 722 | SET CLOSE 23 | Select Adenine to cell |
| 723 | SET CLOSE 24 | Select Thymine to cell |
| 724 | SET OPEN 28 | Drive syringe up |
| 725 | INTVL TM 000.05 | Deliver MSNT, Adenine & Thymine to synthesis cell |
| 726 | SET OPEN 25 | Select MSNT from vial |
| 727 | SET OPEN 23 | Select Adenine from vial |
| 728 | SET OPEN 24 | Select Thymine from vial |
| 729 | SET CLOSE 28 | Refill syringes from vials |

-continued

| | | |
|---|---|---|
| 730 | INTVL TM 000.05 | Allow 3 secs. for refill |
| 731 | SET CLOSE 25 | Select MSNT for push to cell to clear dead volume |
| 732 | SET OPEN 28 | Drive syringe up |
| 733 | INTVL TM 000.05 | Allow three seconds to deliver MSNT |
| 734 | SET OPEN 25 | Select MSNT vial |
| 735 | INC LP CNT 9999 | Add 1 to counter 9. Count = # of steps done in sequence |
| 736 | DISP LP CNT 9 | Display # steps in sequence completed |
| 737 | INTVL TM 025.00 | Wait 25.00 minutes for reaction, (may need altering) |
| 738 | RETURN 0 | Return from subroutine |

| PROGRAMMABLE PARAMETER: | STEP | ENTRY |
|---|---|---|
| More syringe fill/discharge time | 725 730 733 | INTVL TM (TTT.TT) |
| Longer reaction time Time = TTT.TT | 737 | INTVL TM (TTT.TT) |

ADD C&G

| STEP | COMMAND | PURPOSE |
|---|---|---|
| 740 | GO SUBRTN 950 | Charge syringe |
| 741 | SET CLOSE 25 | Select MSNT to cell |
| 742 | SET CLOSE 22 | Select Cytosine to cell |
| 743 | SET CLOSE 21 | Select Guanine to cell |
| 744 | SET OPEN 28 | Drive syringe up |
| 745 | INTVL TM 000.05 | Deliver MSNT, cytosine & guanine to cell |
| 746 | SET OPEN 25 | MSNT syringe to vial |
| 747 | SET OPEN 22 | Cytosine syringe to vial |
| 748 | SET OPEN 21 | Guanine syringe to vial |
| 749 | SET OPEN 28 | Drive syringe down to refill |
| 750 | INTVL TM 000.05 | Refill all syringes |
| 751 | SET CLOSE 25 | Select MSNT to deliver to cell |
| 752 | SET OPEN 28 | Drive syringes up |
| 753 | INTVL TM 000.05 | Deliver MSNT to cell and clear dead volume |
| 754 | SET OPEN 25 | MSNT syringe selected to vial |
| 755 | INC LP CNT 9999 | Add 1 to loop counter 9 |
| 756 | DISP LP CNT | Count in 9 now = total # couplings |
| 757 | INTVL TM 025.00 | 25 min. reaction time (may need altering) |
| 758 | RETURN 0 | Return from subroutine |

| PROGRAMMABLE PARAMETER: | STEP | ENTRY |
|---|---|---|
| More syringe fill/discharge time | 745 750 | INTVL TM (TTT.TT) |
| Longer reaction time Time = TTT.TT | 757 | INTVL TM (TTT.TT) |

ADD C&T

| STEP | COMMAND | PURPOSE |
|---|---|---|
| 760 | GO SUBRTN 950 | Charge syringes |
| 761 | SET CLOSE 25 | Select MSNT to cell |
| 762 | SET CLOSE 22 | Select cytisone to cell |
| 763 | SET CLOSE 24 | Select thymine to cell |
| 764 | SET OPEN 28 | Drive syringe up |
| 765 | INTVL TM 000.005 | Deliver MSNT, Cytosine & Thymine to synthesis cell |
| 766 | SET OPEN 25 | MSNT syringe to vial |
| 767 | SET OPEN 22 | Cytosine syringe to vial |
| 768 | SET OPEN 24 | Thymine syringe to vial |
| 769 | SET CLOSE 28 | Drive syringe down to refill |
| 770 | INTVL TM 000.05 | Refill all syringes |
| 771 | SET CLOSE 25 | Select MSNT to deliver to cell |
| 772 | SET OPEN 28 | Drive syrings up |
| 773 | INTVL TM 000.05 | Deliver MSNT to cell and clear dead volume |
| 774 | SET OPEN 25 | MSNT syringe selected to vial |
| 775 | INC LP CNT 9999 | Add 1 to loop counter 9 |
| 776 | DISP LP CNT 9 | Count in 9 now = total # of couplings |
| 777 | INTVL TM 025.00 | 25 min. reaction time (may need altering) |
| 778 | RETURN 0 | Return from subroutine |

| PROGRAMMABLE PARAMETERS: | STEP | ENTRY |
|---|---|---|
| More syringe fill/discharge Time | 765 770 773 | INTVL TM (TTT.TT) |
| Longer reaction time. Time = TTT.TT | 777 | INTVL TM (TTT TT) |

ADD G&T

| STEP | COMMAND | PURPOSE |
|---|---|---|
| 780 | GO SUBTRN 950 | Charge syringes |
| 781 | SET CLOSE 25 | Select MSNT to cell |
| 782 | SET CLOSE 21 | Select Guanine to cell |
| 783 | SET CLOSE 24 | Select Thymine to cell |

| 784 | SET OPEN 26 | Drive syringe up |
| 785 | INTVL TM 000.05 | Deliver MSNT, Adenine & Thymine to cell |
| 786 | SET OPEN 25 | Select MSNT from vial |
| 787 | SET CLOSE 21 | Select Guanine from |
| 788 | SET OPEN 24 | Select Thymine from vial |
| 789 | SET CLOSE 28 | Refill syringes from vials |
| 790 | INTVL TM 000.05 | Allow 3 secs. for refill |
| 791 | SET CLOSE 25 | Select MSNT for push to cell to clear dead volume |
| 792 | SET OPEN 28 | Drive syringe up |
| 793 | INTVL TM 000.05 | Allow three seconds to deliver MSNT |
| 794 | SET OPEN 25 | Select MSNT vial |
| 795 | INC LP CNT 999 | Add 1 to counter 9. Count # of steps done in sequence |
| 796 | DISP LP CNT 9 | Display # steps in the sequence completed |
| 797 | INTVL TM 025.00 | Wait 25.00 minutes for reaction (may need altering) |
| 798 | RETURN 0 | Return from subroutine |

| PROGRAMMABLE PARAMETER: | STEP | ENTRY |
|---|---|---|
| More syringe fill/discharge time | 785 790 793 | INTVL TM (TTT.TT) |
| Longer reaction time. Time TTT.TT | 797 | INTVL TM (TTT.TT) |

SYRINGE REFRESH ROUTINE

This subroutine is used to ensure the syringes are primed and that the reagent lines are refreshed from the base and MSNT supply vials. With no valve selected, the syringes merely fill, dispense and fill again from the supply vials. The following sequence is followed in the subroutine:
1. Select syringes
2. Drive syringes down to fill
3. Dispense contents of syringe back to vials
4. Fill syringes prior to selecting which to dispense.

| STEP | COMMAND | PURPOSE |
|---|---|---|
| 950 | SET CLOSE 28 | Drive syringe down to fill |
| 951 | SET OPEN 17 | Select syringes to deliver to cell |
| 952 | INTVL TM 000.05 | Wait 3 sec. for syringes to complete filling |
| 953 | SET OPEN 28 | Drive syringes up - dispense back to vials |
| 954 | INTVL TM 000.05 | Wait 3 sec. for syringes to dispense |
| 955 | SET CLOSE 28 | Drive syringes down to fill prior to cell dispense |
| 956 | INTVL TM 000.05 | 3 sec. for syringes to fill |
| 957 | RETURN 0 | Return from subroutine |

| PROGRAMMABLE PARAMETER: | STEP | COMMAND |
|---|---|---|
| Syringes need more time to fill/dispense Time TTT.TT | 932 934 936 | INTVL TM TTT.TT |

Alternatively the speed adjust on the front of the synthesizer may be used to increase the fill speed and rate of dispensing of the bases and MSNT.

POST REACTION ROUTINES: PHOSPHOTRIESTER METHOD: PYRIDINE WASH/N₂ BLOWDOWN

| STEP | COMMAND | PURPOSE |
|---|---|---|
| 960 | SET CLOSE 26 | Rotate cell flow valve to N₂ blowdown position |
| 961 | INTVL TM 000.20 | Blowdown cell .20 minutes |
| 962 | SET OPEN 26 | Turn off N₂ blowdown |
| 963 | GO SUBRTN 565 | Go through the pyridine wash subroutine at step 565 |
| 964 | RETURN 0 | Return from subroutine |

| PROGRAMMABLE PARAMETER: | STEP | COMMAND |
|---|---|---|
| Longer N₂ Blowdown Time | 941 | INTVL TM TTT.TT |

CAPPING ROUTINE

| STEP | COMMAND | PURPOSE |
|---|---|---|
| 970 | SET CLOSE 17 | Select reagents |
| 971 | SET CLOSE 15 | Select capping reagent #1 |
| 972 | SET CLOSE 16 | Select capping reagent #2 |
| 973 | INTVL TM 001.00 | Allow one minute of flow |
| 974 | SET OPEN 15 | Turn off capping reagent #1 |
| 975 | SET OPEN 16 | Turn off capping reagent #2 |
| 976 | INTVL TM 003.00 | Allow 3 minute reaction time |
| 977 | SET CLOSE 26 | Begin N₂ Backflush of Cell |
| 978 | INTVL TM 000.25 | Allow 15 second backflush |
| 979 | SET OPEN 26 | Turn off N₂ Backflush |
| 980 | PRINT LP CNT 9 | Print number of couplings completed |
| 981 | RETURN 0 | Return from subroutine |

| PROGRAMMABLE PARAMETER: | STEP | COMMAND |
|---|---|---|
| More capping solution volume-flow (3 ml) | 953 | INTVL TM 001.00 |
| More capping time-static | 956 | INTVL TM 003.00 |

END ROUTINE

| STEP | COMMAND | PURPOSE |
|---|---|---|
| 990 | SET OPEN 33 | Turn off cell vibrator |
| 991 | SET CLOSE 35 | Turn off cell temperature |
| 992 | SET LP CNT 99999 | Reset counter 9 to zero |
| 993 | PRINT TIME | Print elapsed time (indicates completion synthesis program) |
| 994 | SET CLOCK 000.00 | Reset Clock |
| 995 | RETURN 0 | Return from Subroutine |

Figure 9:
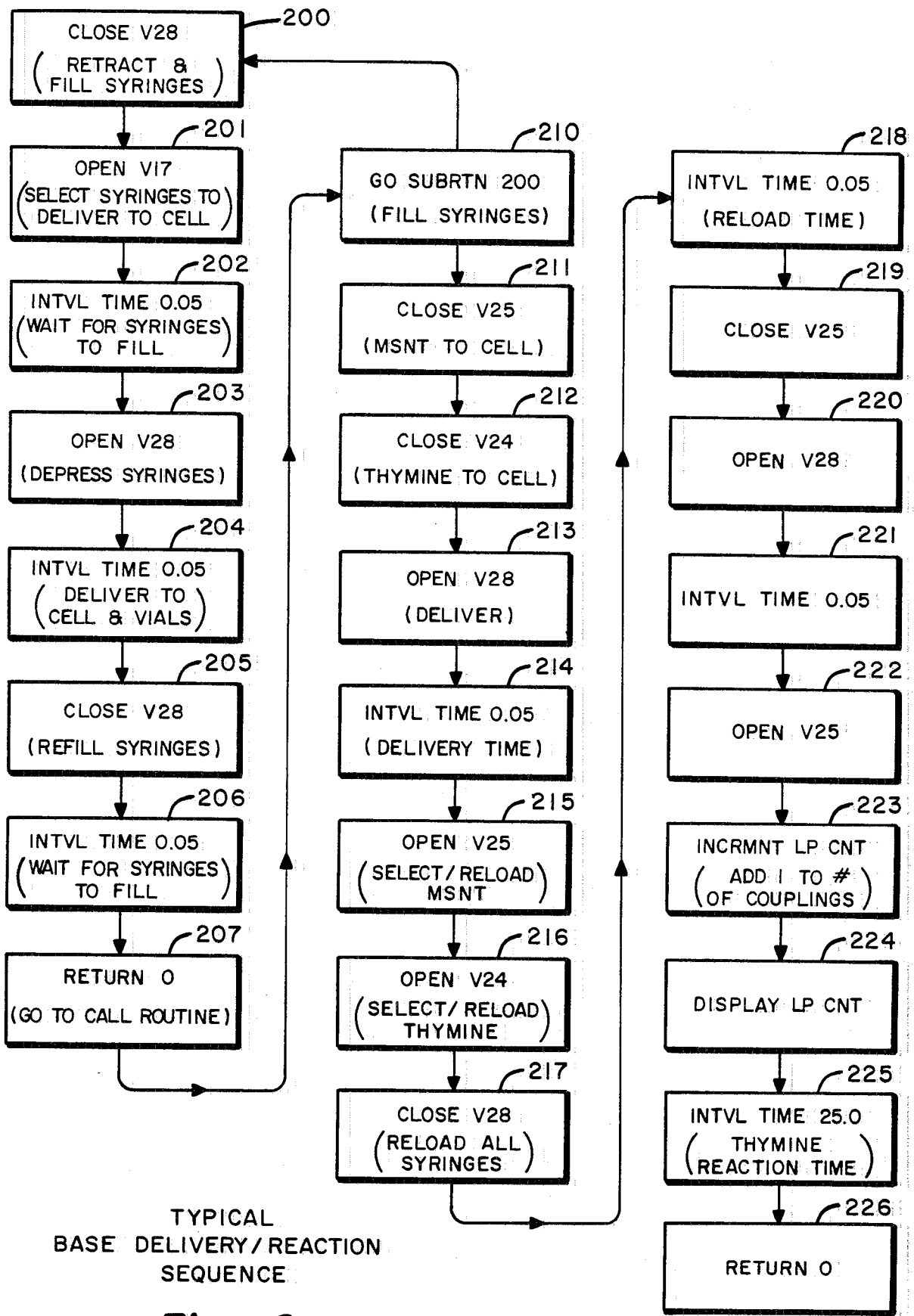
FIG. 9 shows a flow chart of a typical base delivery and reaction sequence.
Figure 10:
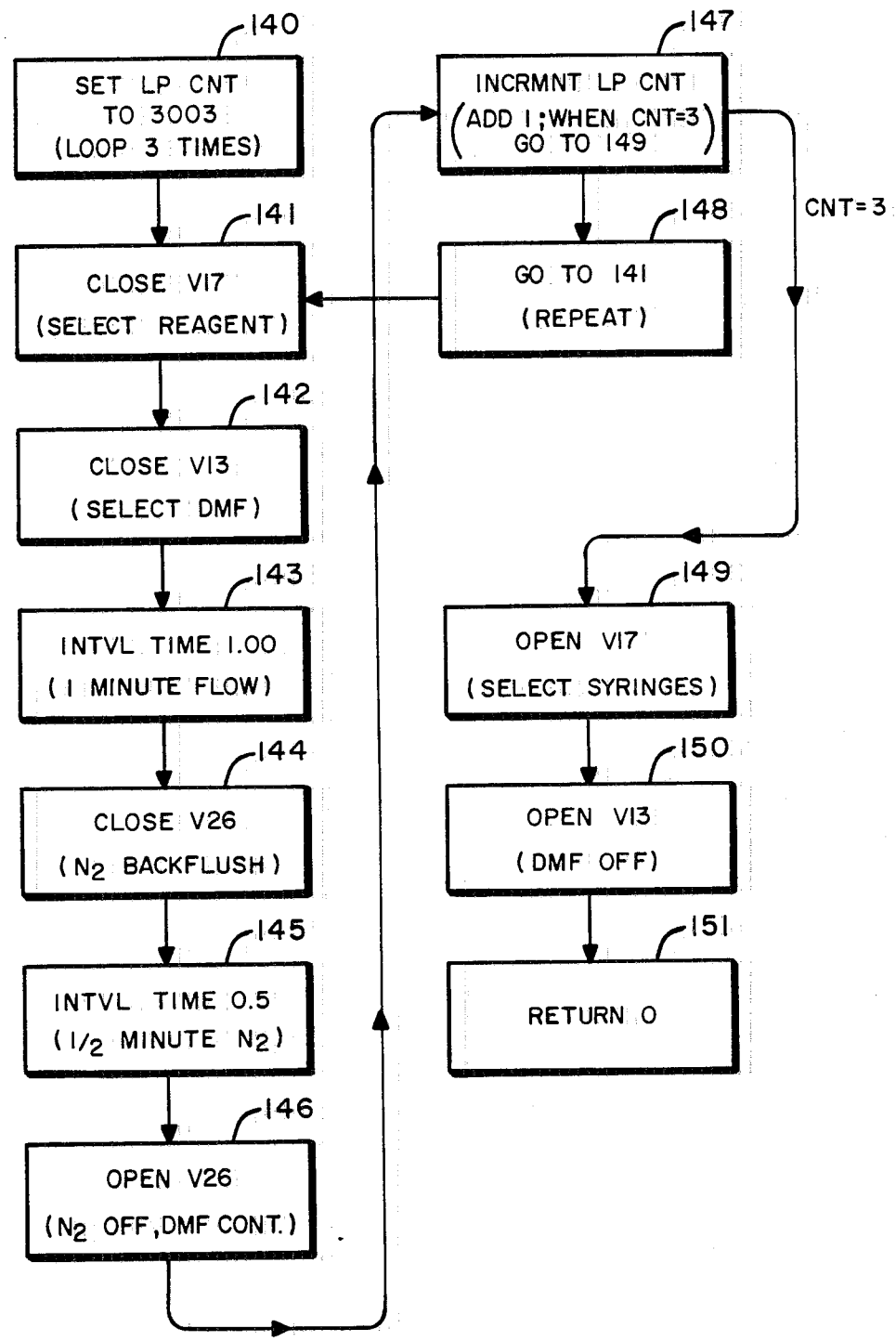
FIG. 10 shows a flow chart of a typical DMF wash sequence.

While Table 4 sets out in great detail each of the various steps performed during each of the various subroutines, attention is also directed to FIGS. 9 and 10 wherein respective flow charts are shown for a typical base delivery and reaction sequence and a typical DMF wash subroutine. Such sequences will be discussed by way of example only, and it is to be recognized that each of the various other subroutines generally proceed in the same fashion as described in Table 4. Before referring thereto though, attention should also be directed to Table 2, since the flow charts of FIGS. 9 and 10 depend upon the I/O assignments previously discussed with respect to FIG. 7.

Referring to FIG. 9, a typical base delivery and reaction sequence begins with the application of an appropriate control signal to I/O group 2, port 8 so as to drive the syringes down and thereby refill the syringes 72 from the vials 50. Next, the controller 12 selects which of the syringes are to deliver their contents to the reaction cell 14 by enabling the associated valve bodies 104. For present purposes though, it will be assumed that thymine is being selected. After waiting approximately three seconds for the syringes to fill, the controller disables port 8 of I/O group 2 so as to drive the syringes up and deliver the contents thereof to their associated vials 50. After waiting approximately 3 seconds, the controller again enables port 8 of I/O Group 2 so as to refill each of the syringes 72. It then again waits for approximately three seconds before repeating the same loop to ensure that the syringes are properly filled before continuing on with its base delivery. It is to be noted that, depending upon the volume of base to be delivered, it may take more or less time to ensure the proper filling of the syringes and therefore the operator may also program an appropriate amount of time to ensure the proper filling of the syringes.

The controller 12, upon ensuring that the syringes 72 are full, next enables port 5 of I/O group 2, as well as port 4, before it again disables port 8 so as to drive the syringe assembly 18 up and thereby deliver the MSNT and thymine to the reaction cell 14. Depending upon the amount of program time, the actual delivery period will vary, but upon delivering the desired chemicals, the controller deselects the valve bodies 104 at ports 4 and 5 before again reloading all of the syringes 72. The controller then again selects the MSNT valve body 104 of port 5 of I/O group 2 and again enables the syringe assembly 18 so as to deliver a second volume of MSNT to the reaction cell, before again refilling all syringes. The coupling counter is then incremented by one and the count is displayed so as to advise the operator of the addition of one unit of thymine to the growing DNA chain on the seeded resin in the reaction cell 14. Depending upon the programmed reaction time, the controller next waits until this time has elapsed before it returns the operator programmed sequence and calls the next subroutine. During the waiting time, the vibrator motor 135 and temperature controller 34 are enabled for appropriate amounts of time so as to enhance the chemical reaction in the cell 14.

Referring next to FIG. 10 and a typcial DMF wash subroutine (which is performed during the base preparation time), the controller 12 upon calling up steps 552 to 564, sets the loop counter for a count of 3 so that the DMF wash will loop or be repeated three times. Next, the controller selects the DMF reagent via ports 3 and 7 of I/O group 1 and permits the DMF to flow for approximately 1 minute or approximately 3 milliliters. Next, the controller closes port 6 of I/O group 2 and admits nitrogen to the flow path and thereby backflushes the reaction cell 14 so as to discharge the DMF remaining in the cell. After approximately a half a minute, the nitrogen is turned off, the loop counter is incremented and the process is repeated. Upon the loop counter reaching a count of 3, which implies the washing of the cell 3 times, the controller exits from the loop and deselects ports 7 and 3 of I/O group 1 so as to deactuate the valve body 104 to the DMF bottle, before executing the Return 0 subroutine. Thereafter, it is to be recalled, that the controller performs a pyridine wash and a THF wash/dry before it proceeds to the next desired base addition subroutine.

In a similar fashion, the above apparatus sequentially proceeds through each of the various subroutines dictated by the programmed chemistry and the operator directed base additions and program parameters, until the desired oligonucleotide sequence has been synthesized in the reaction cell 14. At that time, the apparatus shuts off. Intermediate thereto, though, and depending upon any check points or tests that the operator might desire, the apparatus essentially proceeds as described.

While the present apparatus has been described with respect to its present preferred implementation and various modifications thereof, it is to be recognized that still other equivalent arrangements may suggest themselves to those of skill in the art. It is therefore contemplated that the present invention as described and as claimed hereinafter should be interpreted to include all such equivalent structures as heretofore contemplated or within the spirit and scope of the following claims.

What is claimed is:

1. Oligonucleotide synthesizing apparatus comprising:
a bottom-fed reaction cell for containing substrate supported seed nucleotides;
a plurality of chemical supply reservoirs for containing certain predetermined bases, reagents and solvents to be used in a synthesis process;
means coupled to said chemical supply reservoirs and to said bottom-fed reaction cell for selectively dispensing one or more of said predetermined bases, reagents, and/or solvents at predetermined times and in predetermined controlled volumes, said bases, reagents and/or solvents dispensing means including a plurality of injectors that are simultaneously actuable, whereby selected ones of said injectors dispense to said bottom-fed reaction cell when the injectors are actuated in a first direction, while the nonselected ones of said injectors dispense to said chemical supply reservoirs, and thereby all of said injectors are simultaneously refilled upon actuation in a second direction;
means for programming a plurality of subroutines corresponding to the sequential steps of the nucleotide synthesizing process and storage means for entering and storing said subroutines as programmed;
means for programming, entering and storing a desired oligonucleotide sequence to be synthesized;
processing means responsive to said programmed, entered and stored sequence and said stored subroutines for selectively actuating said dispensing means so as to subject said seed nucleotides to said bases, reagents, and solvents in a sequential fashion and whereby said programmed, entered and stored oligonucleotide sequence is grown in said bottom-fed reaction cell.

2. Apparatus as set forth in claim 1 including means responsive to said processing means and coupled to said bottom-fed cell for vibrating said bottom-fed cell at predetermined times and for predetermined durations, thereby agitating and promoting the growth of said oligonucleotide sequence.

3. Apparatus as set forth in claim 1 including means responsive to said processing means and coupled to said bottom-fed reaction cell for applying heat thereto at predetermined times and for predetermined durations, whereby the growth of said oligonucleotide sequence is promoted.

4. Apparatus as set forth in claim 3 wherein said heating means comprises a heating element fabricated as a film and a temperature controller for automatically maintaining the contents of said bottom-fed reaction cell at a predetermined temperature pursuant to a time schedule.

5. Apparatus as set forth in claim 1 wherein said dispensing means includes a plurality of pneumatically controlled valves that are coupled to said chemical supply reservoirs and to said bottom-fed reaction cell via a plurality of conduits pressurized with a chemically inert gas and which valves are selectively actuable for directing the flow of said bases, reagents, and solvents.

6. Apparatus as set forth in claim 1 wherein said dispensing means includes;
a plurality of syringes, each of which is associated with one of said chemical supply reservoirs;
a plurality of three-way valves, each coupled to one of said syringes and to one of said associated chemical supply reservoirs;
means containably securing said syringes and selectively operable for simultaneously depressing or retracting the plungers associated therewith and whereby upon depression said syringes deliver their associated contents to said chemical supply reservoirs, except for the selected ones of which deliver a corresponding metered volume to said bottom-fed reaction cell and whereby upon retraction of said plungers all of said syringes are simultaneously refilled from said associated chemical supply reservoirs.

7. Apparatus as set forth in claim 1 wherein said bottom-fed reaction cell comprises:
a body member adaptively formed for containing substrate supported seed nucleotides;
means for coupling inlet and outlet conduits thereto;
first and second inserts mountable within a bore formed in said body member and formed so as to in combination form a cavity of a predetermined shape and volume; and
means adjacent to said first and second inserts and to said coupling means for sealing the interfaces therebetween against leakage.

8. Apparatus as set forth in claim 1 including a plurality of bottom-fed reaction cells, each of said bottom-fed reaction cells being coupled to said dispensing means and wherein additional oligonucleotide sequences are grown.

9. Apparatus as set forth in claim 1 including means coupled to said bottom-fed reaction cell for manually admitting bases, reagents and/or solvents thereto independent of said processing means.

10. Apparatus as set forth in claim 1 wherein said plurality of chemical supply reservoirs include at least one chemical supply reservoir having means for manually admitting additional bases, reagents and/or solvents thereto during the operation of said apparatus.

11. Chemical dispensing apparatus for an oligonucleotide synthesizer comprising:
at least one bottom-fed reaction cell having a cavity formed therein and an inlet and outlet opening thereof;
a plurality of pressurized chemical supply reservoirs; containing certain predetermined bases, reagents and solvents;
coupling means including a plurality of syringes coupled to each of said chemical supply reservoirs, each coupling means comprised of a plunger, a syringe body and a nozzle;
means for selectively simultaneously coupling the contents of said bottom-fed reservoirs and syringes to the bottom inlet portion of each of said bottom-fed reaction cells and for removing waste from the top outlet port.

12. Apparatus as set forth in claim 11 including means for engaging more than one of said syringes so as to simultaneously eject a measured amount of bases, reagents and/or solvents from each during a delivery mode and for simultaneously refilling each with a measured amount of bases, reagents and/or solvents during a refilling mode and wherein at least one of said syringes is selectively coupled to each of said bottom-fed reaction cells during said delivery mode, while the others are coupled to said chemical supply reservoirs.

13. Apparatus as set forth in claim 12 wherein the plungers of each of said syringes are coupled to a moving member, while the syringe bodies of each are coupled to a stationary member and the nozzles thereof are each coupled to a stationary valve body;
said apparatus further including means for selectively and pneumatically engaging said moving member in first and second directions whereby said syringes are able to deliver said bases, reagents and/or solvents or are refilled with said bases, reagents and/or solvents.

14. Apparatus as set forth in claim 11 wherein one or more of said chemical supply reservoirs are mounted on a pneumatically controlled platform that may be selectively raised or lowered so as to facilitate the refilling of the chemical supply reservoirs mounted thereon.

15. Apparatus as set forth in claim 11 wherein said coupling means further includes a plurality of valves having inlet ports and outlet ports, said valves being partitioned into predetermined groupings to control the flow of bases, reagents and/or solvents contained within said chemical supply reservoirs, the outlet ports of each of the valves of said groupings being coupled together in a primary manifold to form a primary collective outlet conduit for each of said predetermined groupings, said primary collective outlet conduits further being coupled together in a secondary manifold to form a secondary collective outlet conduit, said secondary collective outlet conduit being coupled to the inlet of said bottom-fed reaction cell.

16. Apparatus as set forth in claim 11 wherein said bottom-fed reaction cell contains one or more removable die members formed so as to in combination create a reaction cavity of a predetermined three dimensional shape and size, whereby the volume and shape of the reaction cavity may be varied upon changing said die.

17. Oligonucleotide synthesizing apparatus comprising:
a bottom-fed reaction cell within which a programmed oligonucleotide sequence is grown;
a plurality of chemical supply reservoirs containing predetermined bases, reagents and solvents used in a synthesis process;
a plurality of dispensing means and valve means, each coupled to at least one of said chemical supply reservoirs, selectively operable for simultaneously dispensing controlled volumes of said bases, reagents and/or solvents to said bottom-fed reaction cell; and
processing means responsive to an operator programmed oligonucleotide sequence and a process defining microprogram for selectively and in a time dependent fashion for simultaneously actuating said dispensing means so as to controllably admit said bases, reagents and solvents forming a reactant mixture through the base of said reaction cell and exhaust spent materials from said reactant mixture from the top of said bottom-fed reaction cell and thereby grow said programmed oligonucleotide sequence.

18. Apparatus as set forth in claim 17 including a plurality of bottom-fed reaction cells wherein each of said bottom-fed reaction cells is coupled to said dispensing means and wherein additional oligonucleotide sequences are independently grown.

19. Apparatus as set forth in claim 17 including means coupled to said bottom-fed reaction cell for manually admitting bases, reagents and/or solve thereto independent of said processing means.

20. Apparatus as set forth in claim 17 wherein said plurality of chemical supply reservoirs include at least one chemical supply reservoir having means for manually admitting additional bases, reagents and/or solvents thereto during the operation of said apparatus.

21. Delivery apparatus for an oligonucleotide synthesizer comprising:
a plurality of syringes, each of which is associated with one of a chemical supply reservoir;
a plurality of three-way valves, each coupled to one of said syringes and to one of said associated chemical supply reservoirs;
means containably securing said syringes and selectively operable for simultaneously depressing or retracting the plungers associated therewith and whereby upon depression said syringes deliver their associated contents to said chemical supply reservoirs, except for the selected ones of which deliver a corresponding metered volume to a bottom-fed reaction cell and whereby upon retraction of said plungers all of said syringes are simultaneously refilled from said associated chemical supply reservoirs.

22. A bottom-fed reaction cell for an oligonucleotide synthesizer comprising:
a body member adaptively formed for containing substrate supported seed nucleotides;
means for coupling inlet and outlet conduits thereto;
first and second inserts mountable within a bore formed in said body member and configured so as to form a cavity of a predetermined shape and volume when mounted within said bore; and
means adjacent to said first and second inserts and to said coupling means for sealing the interfaces therebetween against leakage.

* * * * *

UNITED STATES PATENT AND TRADEMARK OFFICE
CERTIFICATE OF CORRECTION

PATENT NO. : 4,598,049
DATED : July 1, 1986
INVENTOR(S) : Richard J. Zelinka et al It is certified that error appears in the above-identified patent and that said Letters Patent are hereby corrected as shown below:

Column 35, line 1, after "predetermined" insert -- set --.

Column 36, line 68, before "reaction cell" insert -- bottom-fed --.

Column 37, line 15, "solve" should read -- solvents --.

Signed and Sealed this

Twenty-first Day of October, 1986

[SEAL]

Attest:

DONALD J. QUIGG

Attesting Officer

Commissioner of Patents and Trademarks